United States Patent
Li

(10) Patent No.: US 10,081,813 B2
(45) Date of Patent: Sep. 25, 2018

(54) SOYBEAN ATPS PROMOTER AND ITS USE IN CONSTITUTIVE EXPRESSION OF TRANSGENIC GENES IN PLANTS

(71) Applicant: E I DU PONT DE NEMOURS AND COMPANY, Wilmington, DE (US)

(72) Inventor: Zhongsen Li, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 87 days.

(21) Appl. No.: 15/234,436

(22) Filed: Aug. 11, 2016

(65) Prior Publication Data

US 2016/0348121 A1 Dec. 1, 2016

Related U.S. Application Data

(62) Division of application No. 14/344,326, filed as application No. PCT/US2012/055170 on Sep. 13, 2012, now Pat. No. 9,447,424.

(60) Provisional application No. 61/533,819, filed on Sep. 13, 2011.

(51) Int. Cl.
    *C12N 15/82* (2006.01)
    *C12N 9/12* (2006.01)
    *C12Q 1/6895* (2018.01)

(52) U.S. Cl.
    CPC ....... *C12N 15/8216* (2013.01); *C12N 9/1241* (2013.01); *C12N 15/8245* (2013.01); *C12N 15/8247* (2013.01); *C12N 15/8251* (2013.01); *C12N 15/8257* (2013.01); *C12N 15/8261* (2013.01); *C12N 15/8271* (2013.01); *C12N 15/8273* (2013.01); *C12N 15/8274* (2013.01); *C12N 15/8279* (2013.01); *C12N 15/8286* (2013.01); *C12Q 1/6895* (2013.01); *C12Q 2600/13* (2013.01); *C12Q 2600/158* (2013.01)

(58) Field of Classification Search
    None
    See application file for complete search history.

(56) References Cited

U.S. PATENT DOCUMENTS

| | | |
|---|---|---|
| 2007/0283459 A1 | 12/2007 | Byrum et al. |
| 2009/0133159 A1 | 5/2009 | Li |
| 2010/0064390 A1 | 3/2010 | Li |

OTHER PUBLICATIONS

Rossitza Atanassova et al., Functional analysis of the promoter region of a maize (*Zea mays* L.) H3 histone gene in transgenic *Arabidopsis thaliana*, Plant Molecular Biology, 1998, pp. 275-285, vol. 37.
Michael J. Battraw et al., Histochemical analysis of CaMV 35S promoter-β-glucuronidase gene expression in transgenic rice plants, Plant Molecular Biology, 1990, pp. 527-538, vol. 15.
Andrea L. Eveland et al., Digital Gene Expression Signatures for Maize Development, Plant Physiology, Nov. 2010, pp. 1024-1039, vol. 154.
ATP Sulfurylase, NCBI Accession No. AAL74418.2, Jun. 6, 2006.
Glycine max ATP sulfurylase mRNA, complete cds, NCBI Accession No. AF452454.2, Jun. 6, 2006.
Yves Hatzfeld et al., Functional characterization of a gene encoding a fourth ATP sulfurylase isoform from *Arabidopsis thaliana*, Gene, 2000, pp. 51-58, vol. 248.
Sönke Holtorf, Comparison of different constitutive and inducible promoters for the overexpression of transgenes in *Arabidopsis thaliana*, Plant Molecular Biology, 1995, pp. 637-646, vol. 29.
Richard A. Jefferson et al., GUS fusions: β-glucuronidase as a sensitive and versatile gene fusion marker in higher plants, The EMBO Journal, 1987, pp. 3901-3907, vol. 6, No. 13.
Aine L. Plant et al., Regulation of an *Arabidopsis* oleosin gene promoter in transgenic *Brassica napus*, Plant Molecular Biology, 1994, pp. 193-205, vol. 25.
Carol Potenza et al., Targeting Transgene Expression in Research, Agricultural, and Environmental Applications: Promoters Used in Plant Transformation, In Vitro Cell. Dev. Biol.—Plant; Jan.-Feb. 2004, pp. 1-22, vol. 40.
Pallavi Phartiyal et al., Soybean ATP sulfurylase, a homodimeric enzyme involved in sulfur assimilation, is abundantly expressed in roots and induced by cold treatment, 2006, Archives of Biochemistry and Biophysics, pp. 20-29, vol. 450.
Carmen Rotte et al., Differential Subcellular Localization and Expression of ATP Sulfurylase and 5_-Adenylylsulfate Reductase during Ontogenesis of Arabidopsis Leaves Indicates That Cytosolic and Plastid Forms of ATP Sulfurylase May Have Specialized Functions, Plant Physiology, 2000, pp. 715-724, vol. 124.
miRNA Targeted Gene Sequence SEQ ID No. 244, XP002688403, Retrieved from EBI Accession No. AXU86871, Jan. 7, 2010.
International Search Report—PCT/US2012/055170—dated Dec. 18, 2012.

*Primary Examiner* — Phuong T Bui

(57) ABSTRACT

The invention relates to gene expression regulatory sequences from soybean, specifically to the promoter of a soybean ATP sulfurylase (ATPS) and fragments thereof and their use in promoting the expression of one or more heterologous nucleic acid fragments in a tissue-independent or constitutive manner in plants. The invention further discloses compositions, polynucleotide constructs, transformed host cells, transgenic plants and seeds containing the recombinant construct with the promoter, and methods for preparing and using the same.

9 Claims, 10 Drawing Sheets

Specification includes a Sequence Listing.

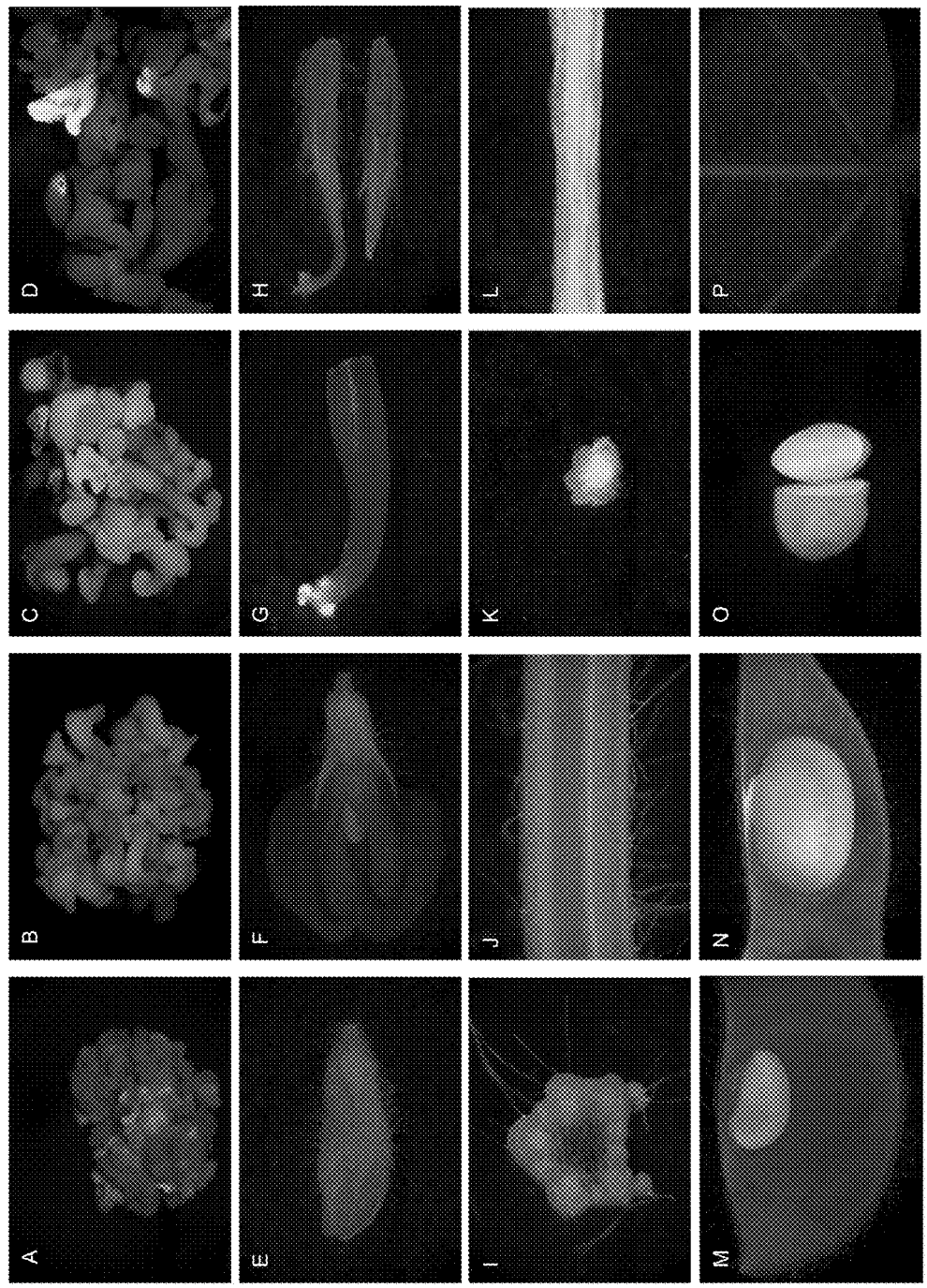

SEQUENCE LISTING

<160> NUMBER OF SEQ ID NOS: 43

<210> SEQ ID NO 1
<211> LENGTH: 1048
<212> TYPE: DNA
<213> ORGANISM: Glycine max
<220> FEATURE:
<221> NAME/KEY: misc_feature
<222> LOCATION: (1)..(1048)
<223> OTHER INFORMATION: GM-ATPS promoter 1048 bp

<400> SEQUENCE: 1

```
cccgggctgg tatattaaaa ttacaaaaaa atttaaataa aaaaatatta aaatatttaa      60
tatattttaa acaataaaac attaaaataa attaacaaca tataaaataa aaccataaaa     120
aatatacatc atattaaata aaattattaa taagtaaaat taaaactatt tatttgaaaa     180
ttaaataaat aattttttta taatttgaaa aaattagaaa aaaaactgta aaaaaaataa     240
aaactattat ttttttaaaa acaaataact ttaaaatttt tttaaaaaaa gttttactac     300
ttcaaatcgt aagaccaaca aaaattaaaa aaaattacaa ctttgaagtt gtaaaagaaa     360
aaaaagttgc ttatgacttt aaaattataa aaaaaataat taatatcata aataatttta     420
tgattttagg taaaaaaaaa tacgaagtcg tggtatcact actcttgact caaaagttgt     480
gagaatggtt acaaattatt ctcttttcac gattatttaa aaaagaccca gttggaaaaa     540
taaaaaaaaa atatacctaa gcagtaaaaa aaaaccctaa taatctctag aaaaacggaa     600
agtagatcga tcataatcca ataaaaagag gaaaaaagaa aacaaaagcc gaaagagaag     660
agatactgcg gtaattaaac aggtcagcaa tgcacacaaa ggtggcaatt attaattatt     720
aattaatacc agtaattgaa agtgaagaaa atgaaaaaac acacagacac acatgggcaa     780
aaaagaagtg tccaggttca tcctcctgaa ccagtctctg tcgaagaagg aaggcccttt     840
atatataaaa acctaaactc gtattgttct gagcaaccca ggttgtctgt tacggattag     900
catcaaagca agttaacaaa atttgggtgc gtcctggatt gacccttttg ccccctctcc     960
ctcaccctcc actaactcct cctttttggt ttttataaag cacattccca atagaggagg    1020
gtccctacac aacacaaccc ttccatgg                                        1048
```

<210> SEQ ID NO 2
<211> LENGTH: 755
<212> TYPE: DNA

<213> ORGANISM: Glycine max
<220> FEATURE:
<221> NAME/KEY: misc_feature
<222> LOCATION: (1)..(755)
<223> OTHER INFORMATION: GM-ATPS promoter 755 bp

<400> SEQUENCE: 2

```
aagtttttact acttcaaatc gtaagaccaa caaaaattaa aaaaaattac aactttgaag      60
ttgtaaaaga aaaaaaagtt gcttatgact ttaaaattat aaaaaaaata attaatatca     120
taaataattt tatgatttta ggtaaaaaaa aatacgaagt cgtggtatca ctactcttga     180
ctcaaaagtt gtgagaatgg ttacaaatta ttctcttttc acgattattt aaaaaagacc     240
cagttggaaa aataaaaaaa aaatatacct aagcagtaaa aaaaaaccct aataatctct     300
agaaaaacgg aaagtagatc gatcataatc caataaaaag aggaaaaaag aaaacaaaag     360
ccgaaagaga agagatactg cggtaattaa acaggtcagc aatgcacaca aaggtggcaa     420
ttattaatta ttaattaata ccagtaattg aaagtgaaga aatgaaaaaa acacacagac     480
acacatgggc aaaaaagaag tgtccaggtt catcctcctg aaccagtctc tgtcgaagaa     540
ggaaggccct ttatatataa aaacctaaac tcgtattgtt ctgagcaacc caggttgtct     600
gttacggatt agcatcaaag caagttaaca aaatttgggt gcgtcctgga ttgaccctt     660
tgccccctct ccctcaccct ccactaactc ctccttttg gttttataa agcacattcc      720
caatagagga gggtccctac acaacacaac ccttc                                755
```

<210> SEQ ID NO 3
<211> LENGTH: 602
<212> TYPE: DNA
<213> ORGANISM: Glycine max
<220> FEATURE:
<221> NAME/KEY: misc_feature
<222> LOCATION: (1)..(602)
<223> OTHER INFORMATION: GM-ATPS promoter 602 bp

<400> SEQUENCE: 3

```
acgaagtcgt ggtatcacta ctcttgactc aaaagttgtg agaatggtta caaattattc      60
tcttttcacg attatttaaa aaagacccag ttggaaaaat aaaaaaaaaa tatacctaag     120
cagtaaaaaa aaaccctaat aatctctaga aaaacggaaa gtagatcgat cataatccaa     180
taaaagagg aaaaaagaaa acaaaagccg aaagagaaga gatactgcgg taattaaaca     240
ggtcagcaat gcacacaaag gtggcaatta ttaattatta attaatacca gtaattgaaa     300
gtgaagaaaa tgaaaaaaca cacagacaca catgggcaaa aagaagtgt ccaggttcat     360
cctcctgaac cagtctctgt cgaagaagga aggcccttta tatataaaaa cctaaactcg     420
tattgttctg agcaacccag gttgtctgtt acggattagc atcaaagcaa gttaacaaaa     480
tttgggtgcg tcctggattg acccttttgc ccctctccc tcaccctcca ctaactcctc     540
ctttttggtt tttataaagc acattcccaa tagaggaggg tccctacaca acacaaccct     600
tc                                                                    602
```

<210> SEQ ID NO 4
<211> LENGTH: 402
<212> TYPE: DNA
<213> ORGANISM: Glycine max
<220> FEATURE:
<221> NAME/KEY: misc_feature
<222> LOCATION: (1)..(402)
<223> OTHER INFORMATION: GM-ATPS promoter 402 bp

<400> SEQUENCE: 4

```
acaaaagccg aaagagaaga gatactgcgg taattaaaca ggtcagcaat gcacacaaag      60
gtggcaatta ttaattatta attaatacca gtaattgaaa gtgaagaaaa tgaaaaaaca     120
cacagacaca catgggcaaa aaagaagtgt ccaggttcat cctcctgaac cagtctctgt     180
cgaagaagga aggcccttta tatataaaaa cctaaactcg tattgttctg agcaacccag     240
gttgtctgtt acggattagc atcaaagcaa gttaacaaaa tttgggtgcg tcctggattg     300
acccttttgc ccctctccc tcaccctcca ctaactcctc cttttggtt tttataaagc       360 acattcccaa tagaggaggg tccctacaca acacaaccct tc                        402
```

```
<210> SEQ ID NO 5
<211> LENGTH: 228
<212> TYPE: DNA
<213> ORGANISM: Glycine max
<220> FEATURE:
<221> NAME/KEY: misc_feature
<222> LOCATION: (1)..(228)
<223> OTHER INFORMATION: GM-ATPS promoter 228 bp

<400> SEQUENCE: 5
```

```
ctctgtcgaa gaaggaaggc cctttatata taaaaaccta aactcgtatt gttctgagca      60
acccaggttg tctgttacgg attagcatca aagcaagtta acaaaatttg ggtgcgtcct     120
ggattgaccc ttttgccccc tctccctcac cctccactaa ctcctccttt ttggttttta     180
taaagcacat tcccaataga ggagggtccc tacacaacac aacccttc                  228
```

```
<210> SEQ ID NO 6
<211> LENGTH: 22
<212> TYPE: DNA
<213> ORGANISM: Artificial sequence
<220> FEATURE:
<223> OTHER INFORMATION: primer, PSO349758-A1

<400> SEQUENCE: 6
```

```
aggttttgggc gaagaaagtg gc                                              22
```

```
<210> SEQ ID NO 7
<211> LENGTH: 25
<212> TYPE: DNA
<213> ORGANISM: Artificial sequence
<220> FEATURE:
<223> OTHER INFORMATION: primer, AP1

<400> SEQUENCE: 7
```

```
gtaatacgac tcactatagg gcacg                                            25
```

```
<210> SEQ ID NO 8
<211> LENGTH: 30
<212> TYPE: DNA
<213> ORGANISM: Artificial sequence
<220> FEATURE:
<223> OTHER INFORMATION: primer, PSO349758-A2

<400> SEQUENCE: 8
```

```
ccatggaagg gttgtgttgt gtagggaccc                                       30
```

```
<210> SEQ ID NO 9
<211> LENGTH: 22
<212> TYPE: DNA
<213> ORGANISM: Artificial sequence
<220> FEATURE:
<223> OTHER INFORMATION: primer, AP2
```

<400> SEQUENCE: 9
ctatagggca cgcgtggtcg ac                                        22

<210> SEQ ID NO 10
<211> LENGTH: 48
<212> TYPE: DNA
<213> ORGANISM: Artificial sequence
<220> FEATURE:
<223> OTHER INFORMATION: Universal GenomeWalker adaptor

<400> SEQUENCE: 10
gtaatacgac tcactatagg gcacgcgtgg tcgacggccc gggctggt            48

<210> SEQ ID NO 11
<211> LENGTH: 24
<212> TYPE: DNA
<213> ORGANISM: Artificial sequence
<220> FEATURE:
<223> OTHER INFORMATION: primer, QC398-A

<400> SEQUENCE: 11
gaagggttgt gttgtgtagg gacc                                      24

<210> SEQ ID NO 12
<211> LENGTH: 28
<212> TYPE: DNA
<213> ORGANISM: Artificial sequence
<220> FEATURE:
<223> OTHER INFORMATION: primer, QC398-S1

<400> SEQUENCE: 12
ccgggctggt atattaaaat tacaaaaa                                  28

<210> SEQ ID NO 13
<211> LENGTH: 31
<212> TYPE: DNA
<213> ORGANISM: Artificial sequence
<220> FEATURE:
<223> OTHER INFORMATION: primer, QC398-S2

<400> SEQUENCE: 13
aagttttact acttcaaatc gtaagaccaa c                              31

<210> SEQ ID NO 14
<211> LENGTH: 28
<212> TYPE: DNA
<213> ORGANISM: Artificial sequence
<220> FEATURE:
<223> OTHER INFORMATION: primer, QC398-S3

<400> SEQUENCE: 14
acgaagtcgt ggtatcacta ctcttgac                                  28

<210> SEQ ID NO 15
<211> LENGTH: 28
<212> TYPE: DNA
<213> ORGANISM: Artificial sequence
<220> FEATURE:
<223> OTHER INFORMATION: primer, PSO349758S

<400> SEQUENCE: 15
acaaaagccg aaagagaaga gatactgc                                  28

<210> SEQ ID NO 16
<211> LENGTH: 22

```
<212> TYPE: DNA
<213> ORGANISM: Artificial sequence
<220> FEATURE:
<223> OTHER INFORMATION: primer, QC398-S4

<400> SEQUENCE: 16
ctctgtcgaa gaaggaaggc cc                                             22

<210> SEQ ID NO 17
<211> LENGTH: 1814
<212> TYPE: DNA
<213> ORGANISM: Glycine max
<220> FEATURE:
<221> NAME/KEY: misc_feature
<222> LOCATION: (1)..(1814)
<223> OTHER INFORMATION: ATPS cDNA PSO349758

<400> SEQUENCE: 17
acggattagc atcaaagcaa gttaacaaaa tttgggtgcg tcctggattg acccttttgc     60
cccctctccc tcaccctcca ctaactcctc cttttggtt tttataaagc acattcccaa    120
tagaggaggg tccctacaca acacaaccct tcaatgacgt ccatggccac tttcttcgcc    180
caaacctcct tcccctccca ctctctctcc aaaaccttcg atacccattt cgcccctgcc    240
ccgaaagtca acgtctttgt gaacttcagg gcgaggaggc acgttggggt gcgagtttcg    300
aacgcgctga tcgaaccaga tggagggaag ctcgtggagc ttgtggtgac ggattttgag    360
agggatttga agaagggtga ggctctttcg ttgccgagga tcaagctctc aaggattgac    420
cttgagtggg tccatgtcct cagcgaagga tgggccacac ccctgaaagg cttcatgaga    480
gaagccgagt tcctccaaac gcttcatttc aactcgctcc gactcgatga tgggtcggtc    540
gtgaacatgt cagtgcccat cgtgctggct attgatgatg cgcagaagca tcggatcggg    600
gataacaaaa aggttgctct ttttgattcc aagggagacc ccgttgcaat tctcaataat    660
attgagattt ataagcatcc taaagaagaa agaatagccc gaacttgggg aaccattgcc    720
cctggcctac cttatgttga acaaactata accaatgctg gaaattggtt gattggggt     780 gacctagagg tcattgaacc aattcagtac aatgatggac ttgatcattt tcgtctatct    840
ccgacacaac tccgtgcaga gttcacaagg cgcaatgcgg atgctgtgtt tgccttccag    900
ctccggaatc ctgttcacaa tggccatgct ttgctaatga ctgacacccg aaagcgcctt    960
cttgagatgg gctataagaa tcctgtcctc ttgcttcatc cacttggagg ctacaccaaa   1020
gctgatgatg tcccacttga ttggcgaatg aagcaacatg agaaggtact tgaggatggt   1080
gttcttgatc cagagacaac tgtggtatcc atattcccat ctcccatgca ctatgctgga   1140
cccacggagg tgcagtggca tgcaaaggct aggatcaatg caggggctaa cttctatatc   1200
gttggtcgtg accccgcagg catgagccat ccagttgaga aaagagatct gtatgatgct   1260
gaccatggaa agaaagtatt gagcatggca ccgggactag agcgtctaaa cattcttcct   1320 ttcaggggttg ctgcatatga caagactcag ggtaaaatgg cattctttga cccttcaagg   1380
cctcaggact tcctgttcat atcaggcaca aagatgcgca cactggcaag gaacaaagaa   1440
agtcctcctg atggatttat gtgccctggt ggatggaagg tgctggttga ttactatgat   1500
agcttagtac tctcaagcaa cggcaaagtg caggaagctg ttccagctta atcttgtatc   1560
atatcataat gtatatatct catgattggg agaaaccta agcttatgta ttctcctgct   1620
aagacatact tcacgaggat cctctggccc aatctaataa taataataaa ttaaaacttt   1680
ggggaggcac aagcacggac acattgcctc tctctgtatg tatggcattt agacagcctc   1740
```

```
ttgcacttat ggtgcaattg tgcatgccaa ctctctgtaa tataatgtgg ttgtgctaag    1800
gatttggttt gatc                                                      1814
```

<210> SEQ ID NO 18
<211> LENGTH: 465
<212> TYPE: PRT
<213> ORGANISM: Glycine max

<400> SEQUENCE: 18

```
Met Thr Ser Met Ala Thr Phe Phe Ala Gln Thr Ser Phe Pro Ser His
1               5                  10                  15

Ser Leu Ser Lys Thr Phe Asp Thr His Phe Ala Pro Ala Pro Lys Val
            20                  25                  30

Asn Val Phe Val Asn Phe Arg Ala Arg Arg His Val Gly Val Arg Val
        35                  40                  45

Ser Asn Ala Leu Ile Glu Pro Asp Gly Gly Lys Leu Val Glu Leu Val
    50                  55                  60

Val Thr Asp Phe Glu Arg Asp Leu Lys Lys Gly Glu Ala Leu Ser Leu
65                  70                  75                  80

Pro Arg Ile Lys Leu Ser Arg Ile Asp Leu Glu Trp Val His Val Leu
                85                  90                  95

Ser Glu Gly Trp Ala Thr Pro Leu Lys Gly Phe Met Arg Glu Ala Glu
            100                 105                 110

Phe Leu Gln Thr Leu His Phe Asn Ser Leu Arg Leu Asp Asp Gly Ser
        115                 120                 125

Val Val Asn Met Ser Val Pro Ile Val Leu Ala Ile Asp Asp Ala Gln
    130                 135                 140

Lys His Arg Ile Gly Asp Asn Lys Lys Val Ala Leu Phe Asp Ser Lys
145                 150                 155                 160

Gly Asp Pro Val Ala Ile Leu Asn Asn Ile Glu Ile Tyr Lys His Pro
                165                 170                 175

Lys Glu Glu Arg Ile Ala Arg Thr Trp Gly Thr Ile Ala Pro Gly Leu
            180                 185                 190

Pro Tyr Val Glu Gln Thr Ile Thr Asn Ala Gly Asn Trp Leu Ile Gly
        195                 200                 205

Gly Asp Leu Glu Val Ile Glu Pro Ile Gln Tyr Asn Asp Gly Leu Asp
    210                 215                 220

His Phe Arg Leu Ser Pro Thr Gln Leu Arg Ala Glu Phe Thr Arg Arg
225                 230                 235                 240

Asn Ala Asp Ala Val Phe Ala Phe Gln Leu Arg Asn Pro Val His Asn
                245                 250                 255

Gly His Ala Leu Leu Met Thr Asp Thr Arg Lys Arg Leu Leu Glu Met
            260                 265                 270

Gly Tyr Lys Asn Pro Val Leu Leu Leu His Pro Leu Gly Gly Tyr Thr
        275                 280                 285

Lys Ala Asp Asp Val Pro Leu Asp Trp Arg Met Lys Gln His Glu Lys
    290                 295                 300

Val Leu Glu Asp Gly Val Leu Asp Pro Glu Thr Thr Val Val Ser Ile
305                 310                 315                 320

Phe Pro Ser Pro Met His Tyr Ala Gly Pro Thr Glu Val Gln Trp His
                325                 330                 335

Ala Lys Ala Arg Ile Asn Ala Gly Ala Asn Phe Tyr Ile Val Gly Arg
            340                 345                 350

Asp Pro Ala Gly Met Ser His Pro Val Glu Lys Arg Asp Leu Tyr Asp
```

```
                355                 360                 365
Ala Asp His Gly Lys Lys Val Leu Ser Met Ala Pro Gly Leu Glu Arg
    370                 375                 380

Leu Asn Ile Leu Pro Phe Arg Val Ala Ala Tyr Asp Lys Thr Gln Gly
385                 390                 395                 400

Lys Met Ala Phe Phe Asp Pro Ser Arg Pro Gln Asp Phe Leu Phe Ile
                405                 410                 415

Ser Gly Thr Lys Met Arg Thr Leu Ala Arg Asn Lys Glu Ser Pro Pro
            420                 425                 430

Asp Gly Phe Met Cys Pro Gly Gly Trp Lys Val Leu Val Asp Tyr Tyr
        435                 440                 445

Asp Ser Leu Val Leu Ser Ser Asn Gly Lys Val Gln Glu Ala Val Pro
    450                 455                 460

Ala
465

<210> SEQ ID NO 19
<211> LENGTH: 5208
<212> TYPE: DNA
<213> ORGANISM: Artificial sequence
<220> FEATURE:
<223> OTHER INFORMATION: plasmid QC274

<400> SEQUENCE: 19
cttaatcgcc ttgcagcaca tccccctttc gccagctggc gtaatagcga agaggcccgc        60
accgatcgcc cttcccaaca gttgcgcagc ctgaatggcg aatggcgcct gatgcggtat       120
tttctcctta cgcatctgtg cggtatttca caccgcatac gtcaaagcaa ccatagtacg       180
cgccctgtag cggcgcatta agcgcggcgg gtgtggtggt tacgcgcagc gtgaccgcta       240
cacttgccag cgccctagcg cccgctcctt tcgctttctt cccttccttt ctcgccacgt       300
tcgccggctt tccccgtcaa gctctaaatc ggggctccc tttagggttc cgatttagtg       360
ctttacggca cctcgacccc aaaaaacttg atttgggtga tggttcacgt agtgggccat       420
cgccctgata cacggttttt cgccctttga cgttggagtc cacgttcttt aatagtggac       480
tcttgttcca aactggaaca cactcaacc ctatctcggg ctattctttt gatttataag       540
ggattttgcc gatttcggcc tattggttaa aaatgagct gatttaacaa aatttaacg       600 cgaatttttaa caaatatta acgtttacaa ttttatggtg cactctcagt acaatctgct       660
ctgatgccgc atagttaagc cagccccgac acccgccaac acccgctgac gcgccctgac       720
gggcttgtct gctcccggca tccgcttaca gacaagctgt gaccgtctcc gggagctgca       780
tgtgtcagag gttttcaccg tcatcaccga aacgcgcgag acgaaagggc ctcgtgatac       840 gcctatttttt ataggttaat gtcatgataa taatggtttc ttagacgtca ggtggcactt       900
ttcggggaaa tgtgcgcgga acccctattt gtttattttt ctaaatacat tcaaatatgt       960
atccgctcat gagacaataa ccctgataaa tgcttcaata atattgaaaa aggaagagta      1020
tgagtattca acatttccgt gtcgccctta ttcccttttt tgcggcattt tgccttcctg      1080
tttttgctca cccagaaacg ctggtgaaag taaaagatgc tgaagatcag ttgggtgcac      1140
gagtgggtta catcgaactg gatctcaaca gcggtaagat ccttgagagt tttcgccccg      1200
aagaacgttt tccaatgatg agcactttta aagttctgct atgtggcgcg gtattatccc      1260
gtattgacgc cgggcaagag caactcggtc gccgcataca ctattctcag aatgacttgg      1320
ttgagtactc accagtcaca gaaaagcatc ttacggatgg catgacagta agagaattat      1380
```

```
gcagtgctgc cataaccatg agtgataaca ctgcggccaa cttacttctg acaacgatcg    1440
gaggaccgaa ggagctaacc gcttttttgc acaacatggg ggatcatgta actcgccttg    1500
atcgttggga accggagctg aatgaagcca taccaaacga cgagcgtgac accacgatgc    1560
ctgtagcaat ggcaacaacg ttgcgcaaac tattaactgg cgaactactt actctagctt    1620
cccggcaaca attaatagac tggatggagg cggataaagt tgcaggacca cttctgcgct    1680
cggcccttcc ggctggctgg tttattgctg ataaatctgg agccggtgag cgtgggtctc    1740
gcggtatcat tgcagcactg gggccagatg gtaagccctc ccgtatcgta gttatctaca    1800
cgacggggag tcaggcaact atggatgaac gaaatagaca gatcgctgag ataggtgcct    1860
cactgattaa gcattggtaa ctgtcagacc aagtttactc atatatactt tagattgatt    1920
taaaacttca ttttttaattt aaaaggatct aggtgaagat cctttttgat aatctcatga    1980
ccaaaatccc ttaacgtgag ttttcgttcc actgagcgtc agaccccgta gaaaagatca    2040
aaggatcttc ttgagatcct ttttttctgc gcgtaatctg ctgcttgcaa acaaaaaaac    2100
caccgctacc agcggtggtt tgtttgccgg atcaagagct accaactctt tttccgaagg    2160
taactggctt cagcagagcg cagataccaa atactgtcct tctagtgtag ccgtagttag    2220
gccaccactt caagaactct gtagcaccgc ctacatacct cgctctgcta atcctgttac    2280
cagtggctgc tgccagtggc gataagtcgt gtcttaccgg gttggactca agacgatagt    2340
taccggataa ggcgcagcgg tcgggctgaa cggggggttc gtgcacacag cccagcttgg    2400
agcgaacgac ctacaccgaa ctgagatacc tacagcgtga gctatgagaa agcgccacgc    2460
ttcccgaagg gagaaaggcg gacaggtatc cggtaagcgg cagggtcgga acaggagagc    2520
gcacgaggga gcttccaggg ggaaacgcct ggtatcttta tagtcctgtc gggtttcgcc    2580
acctctgact tgagcgtcga ttttttgtgat gctcgtcagg ggggcggagc ctatggaaaa    2640
acgccagcaa cgcggccttt ttacggttcc tggccttttg ctggcctttt gctcacatgt    2700
tctttcctgc gttatcccct gattctgtgg ataaccgtat taccgccttt gagtgagctg    2760
ataccgctcg ccgcagccga acgaccgagc gcagcgagtc agtgagcgag gaagcggaag    2820
agcgcccaat acgcaaaccg cctctccccg cgcgttggcc gattcattaa tgcagctggc    2880
acgacaggtt tcccgactgg aaagcgggca gtgagcgcaa cgcaattaat gtgagttagc    2940
tcactcatta ggcaccccag gctttacact ttatgcttcc ggctcgtatg ttgtgtggaa    3000
ttgtgagcgg ataacaattt cacacaggaa acagctatga ccatgattac gccaagcttg    3060
gtaccgagct cggatccact agtaacggcc gccagtgtgc tggaattcgc cttactata    3120 gggcacgcgt ggtcgacggc ccgggctggt atattaaaat tacaaaaaaa tttaaataaa    3180 aaatattaa aatatttaat atattttaaa caataaaaca ttaaaataaa ttaacaacat    3240
ataaaataaa accataaaaa atatacatca tattaaataa aattattaat aagtaaaatt    3300
aaaactattt atttgaaaat taaataaata atttttttat aatttgaaaa aattagaaaa    3360
aaaactgtaa aaaaaataaa aactattatt ttttaaaaa caaataactt taaaatttt    3420 ttaaaaaaag ttttactact tcaaatcgta agaccaacaa aaattaaaaa aaattacaac    3480
tttgaagttg taaagaaaa aaaagttgct tatgacttta aaattataaa aaaataatt    3540 aatatcataa ataattttat gattttaggt aaaaaaaaat acgaagtcgt ggtatcacta    3600
ctcttgactc aaaagttgtg agaatggtta caaattattc tcttttcacg attatttaaa    3660
aaagacccag ttgaaaaaat aaaaaaaaaa tatacctaag cagtaaaaaa aaaccctaat    3720
aatctctaga aaaacggaaa gtagatcgat cataatccaa taaaagagg aaaaaagaaa    3780
```

```
acaaaagccg aaagagaaga gatactgcgg taattaaaca ggtcagcaat gcacacaaag    3840
gtggcaatta ttaattatta attaatacca gtaattgaaa gtgaagaaaa tgaaaaaaca    3900
cacagacaca catgggcaaa aaagaagtgt ccaggttcat cctcctgaac cagtctctgt    3960
cgaagaagga aggcccttta tatataaaaa cctaaactcg tattgttctg agcaacccag    4020
gttgtctgtt acggattagc atcaaagcaa gttaacaaaa tttgggtgcg tcctggattg    4080
acccttttgc cccctctccc tcaccctcca ctaactcctc cttttttggtt tttataaagc    4140
acattcccaa tagaggaggg tccctacaca acacaaccct tccatggccc acagcaagca    4200
cggcctgaag gaggagatga ccatgaagta ccacatggag ggctgcgtga acggccacaa    4260
gttcgtgatc accggcgagg gcatcggcta cccccttcaag ggcaagcaga ccatcaacct    4320
gtgcgtgatc gagggcggcc ccctgccctt cagcgaggac atcctgagcg ccggcttcaa    4380
gtacggcgac cggatcttca ccgagtaccc ccaggacatc gtggactact tcaagaacag    4440
ctgccccgcc ggctacacct ggggccggag cttcctgttc gaggacggcg ccgtgtgcat    4500
ctgtaacgtg gacatcaccg tgagcgtgaa ggagaactgc atctaccaca gagcatctt    4560
caacggcgtg aacttccccg ccgacggccc cgtgatgaag aagatgacca ccaactggga    4620
ggccagctgc gagaagatca tgcccgtgcc taagcagggc atcctgaagg gcgacgtgag    4680
catgtacctg ctgctgaagg acggcggccg gtaccggtgc cagttcgaca ccgtgtacaa    4740
ggccaagagc gtgcccagca gatgcccgga gtggcacttc atccagcaca gctgctgcg    4800
ggaggaccgg agcgacgcca agaaccagaa gtggcagctg accgagcacg ccatcgcctt    4860
ccccagcgcc ctggcctgag agctcgaatt tccccgatcg ttcaaacatt tggcaataaa    4920
gtttcttaag attgaatcct gttgccggtc ttgcgatgat tatcatataa tttctgttga    4980
attacgttaa gcatgtaata attaacatgt aatgcatgac gttatttatg agatgggttt    5040
ttatgattag agtcccgcaa ttatacattt aatacgcgat agaaaacaaa atatagcgcg    5100
caaactagga taaattatcg cgcgcggtgt catctatgtt actagatcgg gaattcactg    5160
gccgtcgttt tacaacgtcg tgactgggaa accctggcg ttacccaa                  5208
```

<210> SEQ ID NO 20
<211> LENGTH: 5298
<212> TYPE: DNA
<213> ORGANISM: Artificial sequence
<220> FEATURE:
<223> OTHER INFORMATION: plasmid QC397

<400> SEQUENCE: 20

```
ccgggtgatt gcggttacat catgtacgga aaataattc taatccttga tttaaatttg      60
aacttgacta tttatttatt ctttatttca ttttgtaaat cattttatgt atctcctggc     120
aagcaatttt atccaccttg caccaacacc ttcgggttcc ataatcaaac caccttaact     180
tcacaccatg ctgtaactca caccgcccag catctccaat gtgaaagaag ctaaaattta     240
ataaacaatc atacgaagca gtgacaaaat accagatggt attaatgctt cgataaaatt     300
aattggaaag tataaaatgg tagaaaataa taaattataa ttaatttaag taagataaaa     360
aataattaaa aactaaaatg ttaaaatttt aaaaaaatta ttttaaataa tatttaaaaa     420
cattaaaaat cattttaaaa aatttatttta tagaacaatt aaataaatat ttcagctaat     480
aaaaaacaaa agcttaccta gccttagaag acaacttgtc caacaattag atgataccca     540
ttgcccttac gttttcttta acatcaatta ttgtttttgt caacaagcta tcttttagtt     600
```

```
ttatttattt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atatttttta    780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaataatt attaaagact     960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagattct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt ttcataaag    1620
attttcagat ccgtttacaa caagccttaa ttgttgattc tgtagtcgta gattaaggtt   1680
tttttcatga actacttcag atccgttaaa caacagcctt atttgttgat acttcagtcg   1740
ttttccaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttttcac gaaattgctt cttgaaatta cgtgatggat tttgattctg   1920
atttatcttg tgattgttga ctctacagcc atggcccagt ccaagcacgg cctgaccaag   1980
gagatgacca tgaagtaccg catggagggc tgcgtggacg gccacaagtt cgtgatcacc   2040
ggcgagggca tcggctaccc cttcaagggc aagcaggcca tcaacctgtg cgtggtggag   2100
ggcggccct tgcccttcgc cgaggacatc ttgtccgccg ccttcatgta cggcaaccgc   2160
gtgttcaccg agtacccca ggacatcgtc gactacttca agaactcctg ccccgccggc   2220
tacacctggg accgctcctt cctgttcgag gacggcgccg tgtgcatctg caacgccgac   2280
atcaccgtga gcgtggagga gaactgcatg taccacgagt ccaagttcta cggcgtgaac   2340
ttccccgccg acggccccgt gatgaagaag atgaccgaca ctgggagcc ctcctgcgag    2400
aagatcatcc ccgtgcccaa gcagggcatc ttgaagggcg acgtgagcat gtacctgctg   2460
ctgaaggacg gtggccgctt gcgctgccag ttcgacaccg tgtacaaggc caagtccgtg   2520
ccccgcaaga tgcccgactg gcacttcatc cagcacaagc tgacccgcga ggaccgcagc   2580
gacgccaaga accagaagtg gcacctgacc gagcacgcca tcgcctccgg ctccgccttg   2640
ccctccggac tcagatctcg actagagtcg aacctagact tgtccatctt ctggattggc   2700
caacttaatt aatgtatgaa ataaaaggat gcacacatag tgcatgcta atcactataa    2760
tgtgggcatc aaagttgtgt gttatgtgta attactagtt atctgaataa aagagaaaga   2820
gatcatccat atttcttatc ctaaatgaat gtcacgtgtc tttataattc tttgatgaac   2880
cagatgcatt tcattaacca aatccatata catataaata ttaatcatat ataattaata   2940
tcaattgggt tagcaaaaca aatctagtct aggtgtgttt tgcgaattct agtggccggc   3000
```

```
ccagctgata tccatcacac tggcggccgc actcgactga attggttccg gcgccagcct    3060
gctttttttgt acaaagttgg cattataaaa aagcattgct tatcaatttg ttgcaacgaa   3120
caggtcacta tcagtcaaaa taaaatcatt atttggggcc cgagcttaag taactaacta   3180
acaggaagag tttgtagaaa cgcaaaaagg ccatccgtca ggatggcctt ctgcttagtt   3240
tgatgcctgg cagtttatgg cgggcgtcct gcccgccacc ctccgggccg ttgcttcaca   3300
acgttcaaat ccgctcccgg cggatttgtc ctactcagga gagcgttcac cgacaaacaa   3360
cagataaaac gaaaggccca gtcttccgac tgagcctttc gttttatttg atgcctggca   3420
gttccctact ctcgcttagt agttagacgt ccccgagatc catgctagcg gtaatacggt   3480
tatccacaga atcaggggat aacgcaggaa agaacatgtg agcaaaaggc cagcaaaagg   3540
ccaggaaccg taaaaaggcc gcgttgctgg cgttttttcca taggctccgc cccccctgacg   3600
agcatcacaa aaatcgacgc tcaagtcaga ggtggcgaaa cccgacagga ctataaagat   3660
accaggcgtt tccccctgga agctccctcg tgcgctctcc tgttccgacc ctgccgctta   3720
ccggatacct gtccgccttt ctcccttcgg gaagcgtggc gctttctcat agctcacgct   3780
gtaggtatct cagttcggtg taggtcgttc gctccaagct gggctgtgtg cacgaacccc   3840
ccgttcagcc cgaccgctgc gccttatccg gtaactatcg tcttgagtcc aacccggtaa   3900
gacacgactt atcgccactg gcagcagcca ctggtaacag gattagcaga gcgaggtatg   3960
taggcggtgc tacagagttc ttgaagtggt ggcctaacta cggctacact agaagaacag   4020
tatttggtat ctgcgctctg ctgaagccag ttaccttcgg aaaaagagtt ggtagctctt   4080
gatccggcaa acaaaccacc gctggtagcg gtggtttttt tgtttgcaag cagcagatta   4140
cgcgcagaaa aaaaggatct caagaagatc ctttgatctt ttctacgggg tctgacgctc   4200
agtggaacgg ggcccaatct gaataatgtt acaaccaatt aaccaattct gattagaaaa   4260
actcatcgag catcaaatga aactgcaatt tattcatatc aggattatca ataccatatt   4320
tttgaaaaag ccgtttctgt aatgaaggag aaaactcacc gaggcagttc cataggatgg   4380
caagatcctg gtatcggtct gcgattccga ctcgtccaac atcaatacaa cctattaatt   4440
tcccctcgtc aaaaataagg ttatcaagtg agaaatcacc atgagtgacg actgaatccg   4500
gtgagaatgg caaaagttta tgcatttctt tccagacttg ttcaacaggc cagccattac   4560
gctcgtcatc aaaatcactc gcatcaacca accgttatt cattcgtgat tgcgcctgag   4620
cgagacgaaa tacgcgatcg ctgttaaaag gacaattaca acaggaatc gaatgcaacc   4680
ggcgcaggaa cactgccagc gcatcaacaa tattttcacc tgaatcagga tattcttcta   4740
atacctggaa tgctgttttt ccggggatcg cagtggtgag taaccatgca tcatcaggag   4800
tacggataaa atgcttgatg gtcggaagag gcataaattc cgtcagccag tttagtctga   4860
ccatctcatc tgtaacatca ttggcaacgc tacctttgcc atgtttcaga acaactctg   4920
gcgcatcggg cttcccatac aagcgataga ttgtcgcacc tgattgcccg acattatcgc   4980
gagcccattt ataccatat aaatcagcat ccatgttgga atttaatcgc ggcctcgacg   5040
tttcccgttg aatatggctc ataacacccc ttgtattact gtttatgtaa gcagacagtt   5100
ttattgttca tgatgatata ttttatctt gtgcaatgta acatcagaga ttttgagaca   5160
cgggccagag ctgcagctgg atggcaaata atgatttat tttgactgat agtgacctgt   5220
tcgttgcaac aaattgataa gcaatgcttt cttataatgc caactttgta caagaaagct   5280
gggtctagat atctcgac                                                 5298
```

<210> SEQ ID NO 21
<211> LENGTH: 4391
<212> TYPE: DNA
<213> ORGANISM: Artificial sequence
<220> FEATURE:
<223> OTHER INFORMATION: plasmid QC398

<400> SEQUENCE: 21

| | | | | | |
|---|---|---|---|---|---|
| atgattttat | tttgactgat | agtgacctgt | tcgttgcaac | aaattgataa | gcaatgcttt | 60 |
| cttataatgc | caactttgta | caagaaagct | gggtctagat | atctcgaccc | gggctggtat | 120 |
| attaaaatta | caaaaaaatt | taaataaaaa | aatattaaaa | tatttaatat | attttaaaca | 180 |
| ataaaacatt | aaaataaatt | aacaacatat | aaaataaaac | cataaaaaat | atacatcata | 240 |
| ttaaataaaa | ttattaataa | gtaaaattaa | aactatttat | ttgaaaatta | aataaataat | 300 |
| tttttttataa | tttgaaaaaa | ttagaaaaaa | aactgtaaaa | aaaataaaaa | ctattatttt | 360 |
| tttaaaaaca | ataaacttta | aaattttttt | aaaaaaagtt | ttactacttc | aaatcgtaag | 420 |
| accaacaaaa | attaaaaaaa | attacaactt | tgaagttgta | aaagaaaaaa | aagttgctta | 480 |
| tgactttaaa | attataaaaa | aataattaa | tatcataaat | aattttatga | ttttaggtaa | 540 |
| aaaaaaatac | gaagtcgtgg | tatcactact | cttgactcaa | aagttgtgag | aatggttaca | 600 |
| aattattctc | ttttcacgat | tatttaaaaa | agacccagtt | ggaaaaataa | aaaaaaaata | 660 |
| tacctaagca | gtaaaaaaaa | accctaataa | tctctagaaa | aacggaaagt | agatcgatca | 720 |
| taatccaata | aaaagaggaa | aaaagaaaac | aaaagccgaa | agagaagaga | tactgcggta | 780 |
| attaaacagg | tcagcaatgc | acacaaaggt | ggcaattatt | aattattaat | taataccagt | 840 |
| aattgaaagt | gaagaaaatg | aaaaaacaca | cagacacaca | tgggcaaaaa | agaagtgtcc | 900 |
| aggttcatcc | tcctgaacca | gtctctgtcg | aagaaggaag | gccctttata | tataaaaacc | 960 |
| taaactcgta | ttgttctgag | caacccaggt | tgtctgttac | ggattagcat | caaagcaagt | 1020 |
| taacaaaatt | tgggtgcgtc | ctggattgac | ccttttgccc | cctctccctc | acctccact | 1080 |
| aactcctcct | ttttggtttt | tataaagcac | attcccaata | gaggagggtc | cctacacaac | 1140 |
| acaacccttc | catggcccag | tccaagcacg | gcctgaccaa | ggagatgacc | atgaagtacc | 1200 |
| gcatggaggg | ctgcgtggac | ggccacaagt | tcgtgatcac | cggcgagggc | atcggctacc | 1260 |
| ccttcaaggg | caagcaggcc | atcaacctgt | gcgtggtgga | gggcggcccc | ttgcccttcg | 1320 |
| ccgaggacat | cttgtccgcc | gccttcatgt | acggcaaccg | cgtgttcacc | gagtaccccc | 1380 |
| aggacatcgt | cgactacttc | aagaactcct | gccccgccgg | ctacacctgg | gaccgctcct | 1440 |
| tcctgttcga | ggacggcgcc | gtgtgcatct | gcaacgccga | catcaccgtg | agcgtggagg | 1500 |
| agaactgcat | gtaccacgag | tccaagttct | acggcgtgaa | cttccccgcc | gacgcccccg | 1560 |
| tgatgaagaa | gatgaccgac | aactgggagc | cctcctgcga | gaagatcatc | cccgtgccca | 1620 |
| agcagggcat | cttgaagggc | gacgtgagca | tgtacctgct | gctgaaggac | ggtgccgct | 1680 |
| tgcgctgcca | gttcgacacc | gtgtacaagg | ccaagtccgt | gccccgcaag | atgcccgact | 1740 |
| ggcacttcat | ccagcacaag | ctgacccgcg | aggaccgcag | cgacgccaag | aaccagaagt | 1800 |
| ggcacctgac | cgagcacgcc | atcgcctccg | gctccgcctt | gccctccgga | ctcagatctc | 1860 |
| gactagagtc | gaacctagac | ttgtccatct | tctggattgg | ccaacttaat | taatgtatga | 1920 |
| aataaaagga | tgcacacata | gtgacatgct | aatcactata | atgtgggcat | caaagttgtg | 1980 |
| tgttatgtgt | aattactagt | tatctgaata | aaagagaaag | agatcatcca | tatttcttat | 2040 |
| cctaaatgaa | tgtcacgtgt | ctttataatt | ctttgatgaa | ccagatgcat | ttcattaacc | 2100 |

```
aaatccatat acatataaat attaatcata tataattaat atcaattggg ttagcaaaac    2160
aaatctagtc taggtgtgtt ttgcgaattc tagtggccgg cccagctgat atccatcaca    2220
ctggcggccg cactcgactg aattggttcc ggcgccagcc tgcttttttg tacaaagttg    2280
gcattataaa aaagcattgc ttatcaattt gttgcaacga acaggtcact atcagtcaaa    2340
ataaaatcat tatttggggc ccgagcttaa gtaactaact aacaggaaga gtttgtagaa    2400
acgcaaaaag gccatccgtc aggatggcct tctgcttagt ttgatgcctg gcagtttatg    2460
gcgggcgtcc tgcccgccac cctccgggcc gttgcttcac aacgttcaaa tccgctcccg    2520
gcggatttgt cctactcagg agagcgttca ccgacaaaca acagataaaa cgaaaggccc    2580
agtcttccga ctgagccttt cgttttattt gatgcctggc agttccctac tctcgcttag    2640
tagttagacg tccccgagat ccatgctagc ggtaatacgg ttatccacag aatcaggggga    2700 taacgcagga agaacatgtg agcaaaaggc cagcaaaagc caggaaccg taaaaaggc     2760 cgcgttgctg gcgttttcc ataggctccg ccccctgac gagcatcaca aaaatcgacg     2820
ctcaagtcag aggtggcgaa acccgacagg actataaaga taccaggcgt ttccccctgg    2880
aagctccctc gtgcgctctc ctgttccgac cctgccgctt accggatacc tgtccgcctt    2940
tctcccttcg ggaagcgtgg cgctttctca tagctcacgc tgtaggtatc tcagttcggt    3000
gtaggtcgtt cgctccaagc tgggctgtgt gcacgaaccc cccgttcagc ccgaccgctg    3060
cgccttatcc ggtaactatc gtcttgagtc aacccggta agacacgact tatcgccact    3120
ggcagcagcc actggtaaca ggattagcag agcgaggtat gtaggcggtg ctacagagtt    3180
cttgaagtgg tggcctaact acggctacac tagaagaaca gtatttggta tctgcgctct    3240
gctgaagcca gttaccttcg gaaaaagagt tggtagctct tgatccggca acaaaccac     3300 cgctggtagc ggtggttttt ttgtttgcaa gcagcagatt acgcgcagaa aaaaaggatc    3360
tcaagaagat cctttgatct ttctacgg gtctgacgct cagtggaacg gggcccaatc      3420
tgaataatgt tacaaccaat taaccaattc tgattagaaa aactcatcga gcatcaaatg    3480
aaactgcaat ttattcatat caggattatc aataccatat tttgaaaaaa gccgtttctg    3540
taatgaagga gaaaactcac cgaggcagtt ccataggatg caagatcct ggtatcggtc     3600 tgcgattccg actcgtccaa catcaataca acctattaat ttcccctcgt caaaaataag    3660
gttatcaagt gagaaatcac catgagtgac gactgaatcc ggtgagaatg gcaaaagttt    3720
atgcatttct ttccagactt gttcaacagg ccagccatta cgctcgtcat caaaatcact    3780
cgcatcaacc aaaccgttat tcattcgtga ttgcgcctga gcgagacgaa atacgcgatc    3840
gctgttaaaa ggacaattac aaacaggaat cgaatgcaac cggcgcagga acactgccag    3900
cgcatcaaca atattttcac ctgaatcagg atattcttct aatacctgga atgctgtttt    3960
tccggggatc gcagtggtga gtaaccatgc atcatcagga gtacggataa aatgcttgat    4020
ggtcggaaga ggcataaatt ccgtcagcca gtttagtctg accatctcat ctgtaacatc    4080
attggcaacg ctacctttgc catgtttcag aaacaactct ggcgcatcgg gcttcccata    4140
caagcgatag attgtcgcac ctgattgccc gacattatcg cgagcccatt tatacccata    4200
taaatcagca tccatgttgg aatttaatcg cggcctcgac gtttcccgtt gaatatggct    4260
cataacaccc cttgtattac tgtttatgta agcagacagt tttattgttc atgatgatat    4320
atttttatct tgtgcaatgt aacatcagag attttgagac acgggccaga gctgcagctg    4380
gatggcaaat a                                                         4391
```

<210> SEQ ID NO 22
<211> LENGTH: 8406
<212> TYPE: DNA
<213> ORGANISM: Artificial sequence
<220> FEATURE:
<223> OTHER INFORMATION: plasmid QC586

<400> SEQUENCE: 22

| | | | | | |
|---|---|---|---|---|---|
| aacatattct | caataaaccc | tttagggaaa | taggccaggt | tttcaccgta | acacgccaca | 60 |
| tcttgcgaat | atatgtgtag | aaactgccgg | aaatcgtcgt | ggtattcact | ccagagcgat | 120 |
| gaaaacgttt | cagtttgctc | atggaaaacg | gtgtaacaag | ggtgaacact | atcccatatc | 180 |
| accagctcac | cgtctttcat | tgccatacgg | aattccggat | gagcattcat | caggcgggca | 240 |
| agaatgtgaa | taaaggccgg | ataaaacttg | tgcttatttt | tctttacggt | ctttaaaaag | 300 |
| gccgtaatat | ccagctgaac | ggtctggtta | taggtacatt | gagcaactga | ctgaaatgcc | 360 |
| tcaaaatgtt | ctttacgatg | ccattgggat | atatcaacgg | tggtatatcc | agtgattttt | 420 |
| ttctccattt | tagcttcctt | agctcctgaa | aatctcgacg | gatcctaact | caaaatccac | 480 |
| acattatacg | agccggaagc | ataaagtgta | aagcctgggg | tgcctaatgc | ggccgccaat | 540 |
| atgactggat | atgttgtgtt | ttacagtatt | atgtagtctg | ttttttatgc | aaaatctaat | 600 |
| ttaatatatt | gatatttata | tcattttacg | tttctcgttc | agcttttttg | tacaaacttg | 660 |
| ttgatggggt | taacatatca | taacttcgta | taatgtatgc | tatacgaagt | tataggcctg | 720 |
| gatcttcgag | gtcgacggta | tcgataagct | tagcctaagt | acgtactcaa | aatgccaaca | 780 |
| aataaaaaaa | aagttgcttt | aataatgcca | aaacaaatta | ataaaacact | tacaacaccg | 840 |
| gatttttttt | aattaaaatg | tgccatttag | gataaatagt | taatattttt | aataattatt | 900 |
| taaaaagccg | tatctactaa | aatgattttt | atttggttga | aaatattaat | atgtttaaat | 960 |
| caacacaatc | tatcaaaatt | aaactaaaaa | aaaataagt | gtacgtggtt | aacattagta | 1020 |
| cagtaatata | agaggaaaat | gagaaattaa | gaaattgaaa | gcgagtctaa | ttttaaatt | 1080 |
| atgaacctgc | atatataaaa | ggaaagaaag | aatccaggaa | gaaaagaaat | gaaaccatgc | 1140 |
| atggtcccct | cgtcatcacg | agtttctgcc | atttgcaata | gaaacactga | acacccttc | 1200 |
| tctttgtcac | ttaattgaga | tgccgaagcc | acctcacacc | atgaacttca | tgaggtgtag | 1260 |
| cacccaaggc | ttccatagcc | atgcatactg | aagaatgtct | caagctcagc | acctacttc | 1320 |
| tgtgacgtgt | ccctcattca | ccttcctctc | ttccctataa | ataaccacgc | tcaggttct | 1380 |
| ccgcttcaca | actcaaacat | tctctccatt | ggtccttaaa | cactcatcag | tcatcaggat | 1440 |
| ccaccatgtc | caacttgttg | actgttcacc | agaacttgcc | tgccctccct | gtggatgcta | 1500 |
| cctccgacga | ggtgcgcaag | aacctgatgg | acatgttccg | tgacagacag | gcattctccg | 1560 |
| agcacacttg | gaagatgctc | ctctctgttt | gccgctcttg | ggctgcttgg | tgcaagctca | 1620 |
| acaacagaaa | gtggtttcct | gctgagcctg | aggacgtgag | agactacctc | ctctacttgc | 1680 |
| aagctcgcgg | tctttgccgtg | aagactattc | agcagcatct | gggtcagctc | aacatgttgc | 1740 |
| accgtcgctc | cgggttgcca | agaccttctg | actcaaacgc | cgtctctttg | gtcatgcgca | 1800 |
| ggattaggaa | agagaacgtt | gacgctgagg | agagggctaa | gcaggccctc | gccttttgaga | 1860 |
| ggacagactt | cgaccaggtc | cgctctttga | tggagaactc | cgacaggtgc | caggacatcc | 1920 |
| gtaacctcgc | tttcttgggc | attgcttaca | acactttgct | caggatcgcc | gagatcgcca | 1980 |
| ggatcagagt | gaaggacatc | tcaaggactg | acgtggaaa | aatgctcatc | cacatcgac | 2040 |
| gcactaagac | tctcgtctcc | accgctggag | tcgagaaggc | cctcagtctg | ggagtgacta | 2100 |

```
agctcgtgga gagatggatc agtgtgagtg gcgtcgctga cgaccctaac aactacctct    2160
tctgcagagt gaggaagaac ggtgtggctg caccttcagc tacctcccag ctctccacca    2220
gagctctcga gggcatcttc gaggctactc acaggctcat ctatggtgcc aaggacgact    2280
ccggacaaag atatctggca tggtctggac actccgctcg cgtcggtgct gctagagata    2340
tggctagggc tggagtgtcc atccctgaga tcatgcaagc tggagggtgg accaacgtga    2400
acatcgtgat gaactacatc aggaacctgg actctgagac tggcgctatg gttagactcc    2460
tcgaggacgg agactgaggt accacatggt taacctagac ttgtccatct tctggattgg    2520
ccaacttaat taatgtatga ataaaagga tgcacacata gtgacatgct aatcactata     2580
atgtgggcat caaagttgtg tgttatgtgt aattactagt tatctgaata aagagaaag     2640
agatcatcca tatttcttat cctaaatgaa tgtcacgtgt ctttataatt ctttgatgaa    2700
ccagatgcat ttcattaacc aaatccatat acatataaat attaatcata tataattaat    2760
atcaattggg ttagcaaaac aaatctagtc taggtgtgtt ttgcgaatgc ggccaaacag    2820
tcgactctag agatccgtca acatggtgga gcacgacact ctcgtctact ccaagaatat    2880
caaagataca gtctcagaag accaaagggc tattgagact tttcaacaaa gggtaatatc    2940
gggaaacctc ctcggattcc attgcccagc tatctgtcac ttcatcaaaa ggacagtaga    3000
aaaggaaggt ggcacctaca aatgccatca ttgcgataaa ggaaaggcta tcgttcaaga    3060
tgcctctgcc gacagtggtc ccaaagatgg acccccaccc acgaggagca tcgtggaaaa    3120
agaagacgtt ccaaccacgt cttcaaagca agtggattga tgtgatgatc ctatgcgtat    3180
ggtatgacgt gtgttcaaga tgatgacttc aaacctacct atgacgtatg gtatgacgtg    3240
tgtcgactga tgacttagat ccactcgagc ggctataaat acgtacctac gcaccctgcg    3300
ctaccatccc tagagctgca gcttattttt acaacaatta ccaacaacaa caaacaacaa    3360
acaacattac aattactatt tacaattaca gtcgaccccct agtccatgaa aaagcctgaa    3420
ctcaccgcga cgtctgtcga aagtttctg atcgaaaagt tcgacagcgt ctccgacctg    3480
atgcagctct cggagggcga agaatctcgt gctttcagct tcgatgtagg agggcgtgga    3540
tatgtcctgc gggtaaatag ctgcgccgat ggtttctaca aagatcgtta tgtttatcgg    3600
cactttgcat cggccgcgct cccgattccg gaagtgcttg acattgggga attcagcgag    3660
agcctgacct attgcatctc ccgccgtgca cagggtgtca cgttgcaaga cctgcctgaa    3720
accgaactgc ccgctgttct gcagccggtc gcggaggcca tggatgcgat cgctgcggcc    3780
gatcttagcc agacgagcgg gttcggccca ttcggaccgc aaggaatcgg tcaatacact    3840
acatggcgtg atttcatatg cgcgattgct gatccccatg tgtatcactg gcaaactgtg    3900
atggacgaca ccgtcagtgc gtccgtcgcg caggctctcg atgagctgat gctttgggcc    3960
gaggactgcc ccgaagtccg gcacctcgtg cacgcggatt tcggctccaa caatgtcctg    4020
acggacaatg gccgcataac agcggtcatt gactggagcg aggcgatgtt cggggattcc    4080
caatacgagg tcgccaacat cttcttctgg aggccgtggt tggcttgtat ggagcagcag    4140
acgcgctact cgagcggag gcatccggag cttgcaggat cgccgcggct ccgggcgtat    4200
atgctccgca ttggtcttga ccaactctat cagagcttgg ttgacggcaa tttcgatgat    4260
gcagcttggg cgcagggtcg atgcgacgca atcgtccgat ccggagccgg gactgtcggg    4320
cgtacacaaa tcgcccgcag aagcgcggcc gtctggaccg atggctgtgt agaagtactc    4380
gccgatagtg gaaaccgacg ccccagcact cgtccgaggg caaaggaata gtgaggtacc    4440
```

```
taaagaagga gtgcgtcgaa gcagatcgtt caaacatttg gcaataaagt ttcttaagat    4500
tgaatcctgt tgccggtctt gcatgatta tcatataatt tctgttgaat tacgttaagc     4560
atgtaataat taacatgtaa tgcatgacgt tatttatgag atgggttttt atgattagag    4620
tcccgcaatt atacatttaa tacgcgatag aaaacaaaat atagcgcgca aactaggata    4680
aattatcgcg cgcggtgtca tctatgttac tagatcgatg tcgacccatc gaattaacat    4740
atcataactt cgtataatgt atgctatacg aagttatagg cctggatcca ctagttctag    4800
agcggccgct cgaggggggg cccggtaccg gcgcgccgtt ctatagtgtc acctaaatcg    4860
tatgtgtatg atacataagg ttatgtatta attgtagccg cgttctaacg acaatatgtc    4920
catatggtgc actctcagta caatctgctc tgatgccgca tagttaagcc agccccgaca    4980
cccgccaaca cccgctgacg cgccctgacg ggcttgtctg ctcccggcat ccgcttacag    5040
acaagctgtg accgtctccg ggagctgcat gtgtcagagg ttttcaccgt catcaccgaa    5100
acgcgcgaga cgaaagggcc tcgtgatacg cctattttta taggttaatg tcatgaccaa    5160
aatcccttaa cgtgagtttt cgttccactg agcgtcagac cccgtagaaa agatcaaagg    5220
atcttcttga gatccttttt ttctgcgcgt aatctgctgc ttgcaaacaa aaaaaccacc    5280
gctaccagcg gtggtttgtt tgccggatca agagctacca actctttttc cgaaggtaac    5340
tggcttcagc agagcgcaga taccaaatac tgtccttcta gtgtagccgt agttaggcca    5400
ccacttcaag aactctgtag caccgcctac atacctcgct ctgctaatcc tgttaccagt    5460
ggctgctgcc agtggcgata agtcgtgtct taccggggttg gactcaagac gatagttacc    5520
ggataaggcg cagcggtcgg gctgaacggg gggttcgtgc acacagccca gcttggagcg    5580
aacgacctac accgaactga gatacctaca gcgtgagcat tgagaaagcg ccacgcttcc    5640
cgaagggaga aaggcggaca ggtatccggt aagcggcagg gtcggaacag gagagcgcac    5700
gagggagctt ccagggggaa acgcctggta tctttatagt cctgtcgggt ttcgccacct    5760
ctgacttgag cgtcgatttt tgtgatgctc gtcagggggg cggagcctat ggaaaaacgc    5820
cagcaacgcg gcctttttac ggttcctggc cttttgctgg ccttttgctc acatgttctt    5880
tcctgcgtta tcccctgatt ctgtggataa ccgtattacc gcctttgagt gagctgatac    5940
cgctcgccgc agccgaacga ccgagcgcag cgagtcagtg agcgaggaag cggaagagcg    6000
cccaatacgc aaaccgcctc tccccgcgcg ttggccgatt cattaatgca ggttgatcag    6060
atctcgatcc cgcgaaatta atacgactca ctatagggag accacaacgg tttccctcta    6120
gaaataattt tgtttaactt taagaaggag atatacccat ggaaaagcct gaactcaccg    6180
cgacgtctgt cgagaagttt ctgatcgaaa agttcgacag cgtctccgac ctgatgcagc    6240
tctcggaggg cgaagaatct cgtgctttca gcttcgatgt aggagggcgt ggatatgtcc    6300
tgcgggtaaa tagctgcgcc gatggtttct acaaagatcg ttatgtttat cggcactttg    6360
catcggccgc gctcccgatt ccggaagtgc ttgacattgg ggaattcagc gagagcctga    6420
cctattgcat ctcccgccgt gcacagggtg tcacgttgca agacctgcct gaaaccgaac    6480
tgcccgctgt tctgcagccg gtcgcggagg ctatggatgc gatcgctgcg gccgatctta    6540
gccagacgag cgggttcggc ccattcggac cgcaaggaat cggtcaatac actacatggc    6600
gtgatttcat atgcgcgatt gctgatcccc atgtgtatca ctggcaaact gtgatggacg    6660
acaccgtcag tgcgtccgtc gcgcaggctc tcgatgagct gatgctttgg gccgaggact    6720
gccccgaagt ccggcacctc gtgcacgcgg atttcggctc caacaatgtc ctgacggaca    6780
atggccgcat aacagcggtc attgactgga gcgaggcgat gttcggggat tcccaatacg    6840
```

```
aggtcgccaa catcttcttc tggaggccgt ggttggcttg tatggagcag cagacgcgct    6900
acttcgagcg gaggcatccg gagcttgcag gatcgccgcg gctccgggcg tatatgctcc    6960
gcattggtct tgaccaactc tatcagagct tggttgacgg caatttcgat gatgcagctt    7020
gggcgcaggg tcgatgcgac gcaatcgtcc gatccggagc cgggactgtc gggcgtacac    7080
aaatcgcccg cagaagcgcg gccgtctgga ccgatggctg tgtagaagta ctcgccgata    7140
gtggaaaccg acgcccagc actcgtccga gggcaaagga atagtgaggt acagcttgga    7200
tcgatccggc tgctaacaaa gcccgaaagg aagctgagtt ggctgctgcc accgctgagc    7260
aataactagc ataaccccct tggggcctcta acgggtctt gaggggtttt ttgctgaaag    7320
gaggaactat atccggatga tcgggcgcgc cggtacccat caaccacttt gtacaagaaa    7380
gctgaacgag aaacgtaaaa tgatataaat atcaatatat taaattagat tttgcataaa    7440
aaacagacta cataatactg taaaacacaa catatccagt cactatggtc gacctgcaga    7500
ctggctgtgt ataagggagc ctgacattta tattccccag aacatcaggt taatggcgtt    7560
tttgatgtca ttttcgcggt ggctgagatc agccacttct tccccgataa cggagaccgg    7620
cacactggcc atatcggtgg tcatcatgcg ccagctttca tccccgatat gcaccaccgg    7680
gtaaagttca cgggagactt tatctgacag cagacgtgca ctggccaggg ggatcaccat    7740
ccgtcgcccg ggcgtgtcaa taatatcact ctgtacatcc acaaacagac gataacggct    7800
ctctctttta taggtgtaaa ccttaaactg catttcacca gccctgttc tcgtcagcaa    7860 aagagccgtt catttcaata aaccgggcga cctcagccat ccttcctga tttcccgctt    7920 tccagcgttc ggcacgcaga cgacgggctt cattctgcat ggttgtgctt accagaccgg    7980
agatattgac atcatatatg ccttgagcaa ctgatagctg tcgctgtcaa ctgtcactgt    8040
aatacgctgc ttcatagcat acctcttttt gacatacttc gggtatacat atcagtatat    8100
attcttatac cgcaaaaatc agcgcgcaaa tacgcatact gttatctggc ttttagtaag    8160
ccggatccag atctttacgc cccgccctgc cactcatcgc agtactgttg taattcatta    8220
agcattctgc cgacatggaa gccatcacaa acggcatgat gaacctgaat cgccagcggc    8280
atcagcacct tgtcgccttg cgtataatat ttgcccatgg tgaaacggg ggcgaagaag    8340 ttgtccatat tggccacgtt taaatcaaaa ctggtgaaac tcacccaggg attggctgag    8400
acgaaa                                                                8406
```

<210> SEQ ID NO 23
<211> LENGTH: 8913
<212> TYPE: DNA
<213> ORGANISM: Artificial sequence
<220> FEATURE:
<223> OTHER INFORMATION: plasmid QC589

<400> SEQUENCE: 23

```
tatccggtaa gcggcagggt cggaacagga gagcgcacga gggagcttcc aggggggaaac    60 gcctggtatc tttatagtcc tgtcgggttt cgccacctct gacttgagcg tcgatttttg    120
tgatgctcgt caggggggcg gagcctatgg aaaaacgcca gcaacgcggc ctttttacgg    180
ttcctggcct tttgctggcc ttttgctcac atgttctttc ctgcgttatc ccctgattct    240
gtggataacc gtattaccgc ctttgagtga gctgataccg ctcgccgcag ccgaacgacc    300
gagcgcagcg agtcagtgag cgaggaagcg gaagagcgcc caatacgcaa accgcctctc    360
cccgcgcgtt ggccgattca ttaatgcagg ttgatcagat ctcgatcccg cgaaattaat    420
```

```
acgactcact ataggaagac cacaacggtt tccctctaga aataattttg tttaacttta    480
agaaggagat atacccatgg aaaagcctga actcaccgcg acgtctgtcg agaagtttct    540
gatcgaaaag ttcgacagcg tctccgacct gatgcagctc tcggagggcg aagaatctcg    600
tgctttcagc ttcgatgtag gagggcgtgg atatgtcctg cgggtaaata gctgcgccga    660
tggtttctac aaagatcgtt atgtttatcg gcactttgca tcggccgcgc tcccgattcc    720
ggaagtgctt gacattgggg aattcagcga gagcctgacc tattgcatct cccgccgtgc    780
acagggtgtc acgttgcaag acctgcctga aaccgaactg cccgctgttc tgcagccggt    840
cgcggaggct atggatgcga tcgctgcggc cgatcttagc cagacgagcg ggttcggccc    900
attcggaccg caaggaatcg gtcaatacac tacatggcgt gatttcatat gcgcgattgc    960
tgatccccat gtgtatcact ggcaaactgt gatggacgac accgtcagtg cgtccgtcgc    1020
gcaggctctc gatgagctga tgctttgggc cgaggactgc cccgaagtcc ggcacctcgt    1080
gcacgcggat ttcggctcca acaatgtcct gacggacaat ggccgcataa cagcggtcat    1140
tgactggagc gaggcgatgt tcggggattc ccaatacgag gtcgccaaca tcttcttctg    1200
gaggccgtgg ttggcttgta tggagcagca gacgcgctac ttcgagcgga ggcatccgga    1260
gcttgcagga tcgccgcggc tccgggcgta tatgctccgc attggtcttg accaactcta    1320
tcagagcttg gttgacggca atttcgatga tgcagcttgg gcgcagggtc gatgcgacgc    1380
aatcgtccga tccggagccg ggactgtcgg gcgtacacaa atcgcccgca gaagcgcggc    1440
cgtctggacc gatggctgtg tagaagtact cgccgatagt ggaaaccgac gccccagcac    1500
tcgtccgagg gcaaaggaat agtgaggtac agcttggatc gatccggctg ctaacaaagc    1560
ccgaaaggaa gctgagttgg ctgctgccac cgctgagcaa taactagcat aaccccttgg    1620
ggcctctaaa cgggtcttga ggggtttttt gctgaaagga gaactatat ccggatgatc    1680 gggcgcgccg gtacccatca accactttgt acaagaaagc tgggtctaga tatctcgacc    1740
cgggctggta tattaaaatt acaaaaaaat ttaaataaaa aatattaaa atatttaata    1800 tattttaaac aataaaacat taaaataaat taacaacata taaaataaaa ccataaaaaa    1860
tatacatcat attaaataaa attattaata agtaaaatta aaactattta tttgaaaatt    1920
aaataaataa tttttttata atttgaaaaa attagaaaaa aaactgtaaa aaaaataaaa    1980
actattattt ttttaaaaac aaataacttt aaaattttt taaaaaagt tttactactt    2040 caaatcgtaa gaccaacaaa aattaaaaaa aattacaact ttgaagttgt aaaagaaaaa    2100
aaagttgctt atgactttaa aattataaaa aaaataatta atatcataaa taattttatg    2160 atttaggta aaaaaaata cgaagtcgtg gtatcactac tcttgactca aaagttgtga    2220
gaatggttac aaattattct cttttcacga ttatttaaaa aagacccagt tggaaaaata    2280 aaaaaaaat atacctaagc agtaaaaaaa aaccctaata atctctagaa aaacggaaag    2340
tagatcgatc ataatccaat aaaaagagga aaaagaaaa caaaagccga aagagaagag    2400
atactgcggt aattaaacag gtcagcaatg cacacaaagg tggcaattat taattattaa    2460
ttaataccag taattgaaag tgaagaaaat gaaaaaacac acagacacac atgggcaaaa    2520
aagaagtgtc caggttcatc ctcctgaacc agtctctgtc gaagaaggaa ggccctttat    2580
atataaaaac ctaaactcgt attgttctga gcaacccagg ttgtctgtta cggattagca    2640
tcaaagcaag ttaacaaaat ttgggtgcgt cctggattga ccttttgcc ccctctccct    2700 cacccctcca c taactcctcc tttttggttt ttataaagca cattcccaat agaggagggt    2760
ccctacacaa cacaacccct tccatggccca gtccaagcac ggcctgacca aggagatgac    2820
```

```
catgaagtac cgcatggagg gctgcgtgga cggccacaag ttcgtgatca ccggcgaggg    2880
catcggctac cccttcaagg gcaagcaggc catcaacctg tgcgtggtgg agggcggccc    2940
cttgcccttc gccgaggaca tcttgtccgc cgccttcatg tacggcaacc gcgtgttcac    3000
cgagtacccc caggacatcg tcgactactt caagaactcc tgccccgccg gctacacctg    3060
ggaccgctcc ttcctgttcg aggacggcgc cgtgtgcatc tgcaacgccg acatcaccgt    3120
gagcgtggag gagaactgca tgtaccacga gtccaagttc tacggcgtga acttccccgc    3180
cgacggcccc gtgatgaaga agatgaccga caactgggag ccctcctgcg agaagatcat    3240
ccccgtgccc aagcagggca tcttgaaggg cgacgtgagc atgtacctgc tgctgaagga    3300
cggtggccgc ttgcgctgcc agttcgacac cgtgtacaag gccaagtccg tgccccgcaa    3360
gatgcccgac tggcacttca tccagcacaa gctgacccgc gaggaccgca gcgacgccaa    3420
gaaccagaag tggcacctga ccgagcacgc catcgcctcc ggctccgcct tgccctccgg    3480
actcagatct cgactagagt cgaacctaga cttgtccatc ttctggattg ccaacttaa    3540
ttaatgtatg aaataaaagg atgcacacat agtgacatgc taatcactat aatgtgggca    3600
tcaaagttgt gtgttatgtg taattactag ttatctgaat aaaagagaaa gagatcatcc    3660
atatttctta tcctaaatga atgtcacgtg tctttataat tctttgatga accagatgca    3720
tttcattaac caaatccata tacatataaa tattaatcat atataattaa tatcaattgg    3780
gttagcaaaa caaatctagt ctaggtgtgt tttgcgaatt ctagtggccg gcccagctga    3840
tatccatcac actggcggcc gcactcgact gaattggttc cggcgccagc ctgcttttt    3900
gtacaaactt gttgatgggg ttaacatatc ataacttcgt ataatgtatg ctatacgaag    3960
ttataggcct ggatcttcga ggtcgacggt atcgataagc ttagcctaag tacgtactca    4020
aaatgccaac aaataaaaaa aaagttgctt taataatgcc aaaacaaatt aataaaacac    4080
ttacaacacc ggatttttt taattaaaat gtgccattta ggataaatag ttaatatttt    4140
taataattat ttaaaagcc gtatctacta aaatgatttt tatttggttg aaaatattaa    4200
tatgtttaaa tcaacacaat ctatcaaaat taaactaaaa aaaaaataag tgtacgtggt    4260
taacattagt acagtaatat aagaggaaaa tgagaaatta agaaattgaa agcgagtcta    4320
attttttaaat tatgaacctg catatataaa aggaaagaaa gaatccagga agaaaagaaa    4380
tgaaaccatg catggtcccc tcgtcatcac gagtttctgc catttgcaat agaaacactg    4440
aaacaccttt ctctttgtca cttaattgag atgccgaagc cacctcacac catgaacttc    4500
atgaggtgta gcacccaagg cttccatagc catgcatact gaagaatgtc tcaagctcag    4560
caccctactt ctgtgacgtg tccctcattc accttcctct cttccctata aataaccacg    4620
cctcaggttc tccgcttcac aactcaaaca ttctctccat tggtccttaa acactcatca    4680
gtcatcagga tccaccatgt ccaacttgtt gactgttcac cagaacttgc ctgccctccc    4740
tgtggatgct acctccgacg aggtgcgcaa gaacctgatg gacatgttcc gtgacagaca    4800
ggcattctcc gagcacactt ggaagatgct cctctctgtt tgccgctctt gggctgcttg    4860
gtgcaagctc aacaacagaa agtggtttcc tgctgagcct gaggacgtga gagactacct    4920
cctctacttg caagctcgcg tcttgccgt gaagactatt cagcagcatc tgggtcagct    4980
caacatgttg caccgtcgct ccgggttgcc aagaccttct gactcaaacg ccgtctcttt    5040
ggtcatgcgc aggattagga aagagaacgt tgacgctgga gagagggcta agcaggccct    5100
cgcctttgag aggacagact tcgaccaggt ccgctctttg atggagaact ccgacaggtg    5160
```

```
ccaggacatc cgtaacctcg ctttcttggg cattgcttac aacactttgc tcaggatcgc   5220
cgagatcgcc aggatcagag tgaaggacat ctcaaggact gacggtggaa gaatgctcat   5280
ccacatcgga cgcactaaga ctctcgtctc caccgctgga gtcgagaagg ccctcagtct   5340
gggagtgact aagctcgtgg agagatggat cagtgtgagt ggcgtcgctg acgaccctaa   5400
caactacctc ttctgcagag tgaggaagaa cggtgtggct gcaccttcag ctacctccca   5460
gctctccacc agagctctcg agggcatctt cgaggctact cacaggctca tctatggtgc   5520
caaggacgac tccggacaaa gatatctggc atggtctgga cactccgctc gcgtcggtgc   5580
tgctagagat atggctaggg ctggagtgtc catccctgag atcatgcaag ctggagggtg   5640
gaccaacgtg aacatcgtga tgaactacat caggaacctg gactctgaga ctggcgctat   5700
ggttagactc ctcgaggacg gagactgagg taccacatgg ttaacctaga cttgtccatc   5760
ttctggattg ccaacttaa ttaatgtatg aaataaaagg atgcacacat agtgacatgc   5820
taatcactat aatgtgggca tcaaagttgt gtgttatgtg taattactag ttatctgaat   5880
aaaagagaaa gagatcatcc atatttctta tcctaaatga atgtcacgtg tctttataat   5940
tctttgatga accagatgca tttcattaac caaatccata tacatataaa tattaatcat   6000
atataattaa tatcaattgg gttagcaaaa caaatctagt ctaggtgtgt tttgcgaatg   6060
cggccaaaca gtcgactcta gagatccgtc aacatggtgg agcacgacac tctcgtctac   6120
tccaagaata tcaaagatac agtctcagaa gaccaaaggg ctattgagac ttttcaacaa   6180
agggtaatat cgggaaacct cctcggattc cattgcccag ctatctgtca cttcatcaaa   6240
aggacagtag aaaaggaagg tggcacctac aaatgccatc attgcgataa aggaaaggct   6300
atcgttcaag atgcctctgc cgacagtggt cccaaagatg gacccccacc cacgaggagc   6360
atcgtggaaa aagaagacgt tccaaccacg tcttcaaagc aagtggattg atgtgatgat   6420
cctatgcgta tggtatgacg tgtgttcaag atgatgactt caaacctacc tatgacgtat   6480
ggtatgacgt gtgtcgactg atgacttaga tccactcgag cggctataaa tacgtaccta   6540
cgcaccctgc gctaccatcc ctagagctgc agcttatttt tacaacaatt accaacaaca   6600
acaaacaaca aacaacatta caattactat ttacaattac agtcgacccc tagtccatga   6660
aaaagcctga actcaccgcg acgtctgtcg agaagtttct gatcgaaaag ttcgacagcg   6720
tctccgacct gatgcagctc tcggagggcg aagaatctcg tgctttcagc ttcgatgtag   6780
gagggcgtgg atatgtcctg cgggtaaata gctgcgccga tggtttctac aaagatcgtt   6840
atgtttatcg gcactttgca tcggccgcgc tcccgattcc ggaagtgctt gacattgggg   6900
aattcagcga gagcctgacc tattgcatct cccgccgtgc acagggtgtc acgttgcaag   6960
acctgcctga aaccgaactg cccgctgttc tgcagccggt cgcggaggcc atggatgcga   7020
tcgctgcggc cgatcttagc cagacgagcg ggttcggccc attcggaccg caaggaatcg   7080
gtcaatacac tacatggcgt gatttcatat gcgcgattgc tgatccccat gtgtatcact   7140
ggcaaactgt gatggacgac accgtcagtg cgtccgtcgc gcaggctctc gatgagctga   7200
tgctttgggc cgaggactgc cccgaagtcc ggcacctcgt gcacgcggat tcggctcca   7260 acaatgtcct gacggacaat ggccgcataa cagcggtcat tgactggagc gaggcgatgt   7320
tcggggattc ccaatacgag gtcgccaaca tcttcttctg gaggccgtgg ttggcttgta   7380
tggagcagca gacgcgctac ttcgagcgga ggcatccgga gcttgcagga tcgccgcggc   7440
tccgggcgta tatgctccgc attggtcttg accaactcta tcagagcttg gttgacggca   7500
atttcgatga tgcagcttgg gcgcagggtc gatgcgacgc aatcgtccga tccggagccg   7560
```

```
ggactgtcgg gcgtacacaa atcgcccgca gaagcgcggc cgtctggacc gatggctgtg    7620
tagaagtact cgccgatagt ggaaaccgac gccccagcac tcgtccgagg gcaaaggaat    7680
agtgaggtac ctaaagaagg agtgcgtcga agcagatcgt tcaaacattt ggcaataaag    7740
tttcttaaga ttgaatcctg ttgccggtct tgcgatgatt atcatataat ttctgttgaa    7800
ttacgttaag catgtaataa ttaacatgta atgcatgacg ttatttatga gatgggtttt    7860
tatgattaga gtcccgcaat tatacattta atacgcgata gaaaacaaaa tatagcgcgc    7920
aaactaggat aaattatcgc gcgcggtgtc atctatgtta ctagatcgat gtcgacccat    7980
cgaattaaca tatcataact tcgtataatg tatgctatac gaagttatag gcctggatcc    8040
actagttcta gagcggccgc tcgagggggg gcccggtacc ggcgcgccgt tctatagtgt    8100
cacctaaatc gtatgtgtat gatacataag gttatgtatt aattgtagcc gcgttctaac    8160
gacaatatgt ccatatggtg cactctcagt acaatctgct ctgatgccgc atagttaagc    8220
cagccccgac acccgccaac acccgctgac gcgccctgac gggcttgtct gctcccggca    8280
tccgcttaca gacaagctgt gaccgtctcc gggagctgca tgtgtcagag gttttcaccg    8340
tcatcaccga aacgcgcgag acgaaagggc ctcgtgatac gcctattttt ataggttaat    8400
gtcatgacca aaatccctta acgtgagttt tcgttccact gagcgtcaga ccccgtagaa    8460
aagatcaaag gatcttcttg agatcctttt tttctgcgcg taatctgctg cttgcaaaca    8520
aaaaaaccac cgctaccagc ggtggtttgt ttgccggatc aagagctacc aactcttttt    8580
ccgaaggtaa ctggcttcag cagagcgcag ataccaaata ctgtccttct agtgtagccg    8640
tagttaggcc accacttcaa gaactctgta gcaccgccta catacctcgc tctgctaatc    8700
ctgttaccag tggctgctgc cagtggcgat aagtcgtgtc ttaccgggtt ggactcaaga    8760
cgatagttac cggataaggc gcagcggtcg ggctgaacgg ggggttcgtg cacacagccc    8820
agcttggagc gaacgaccta caccgaactg agatacctac agcgtgagca ttgagaaagc    8880
gccacgcttc ccgaagggag aaaggcggac agg                                8913
```

<210> SEQ ID NO 24  
<211> LENGTH: 3859  
<212> TYPE: DNA  
<213> ORGANISM: Artificial sequence  
<220> FEATURE:  
<223> OTHER INFORMATION: plasmid QC398-1

<400> SEQUENCE: 24

```
accaccgcta ccagcggtgg tttgtttgcc ggatcaagag ctaccaactc ttttccgaa      60 ggtaactggc ttcagcagag cgcagatacc aaatactgtc cttctagtgt agccgtagtt    120
aggccaccac ttcaagaact ctgtagcacc gcctacatac ctcgctctgc taatcctgtt    180
accagtggct gctgccagtg gcgataagtc gtgtcttacc gggttggact caagacgata    240
gttaccggat aaggcgcagc ggtcgggctg aacgggggt tcgtgcacac agcccagctt     300
ggagcgaacg acctacaccg aactgagata cctacagcgt gagcattgag aaagcgccac    360
gcttcccgaa gggagaaagg cggacaggta tccggtaagc ggcagggtcg gaacaggaga    420
gcgcacgagg gagcttccag gggaaacgc ctggtatctt tatagtcctg tcgggtttcg     480
ccacctctga cttgagcgtc gatttttgtg atgctcgtca ggggggcgga gcctatggaa    540
aaacgccagc aacgcggcct ttttacggtt cctggccttt tgctggcctt ttgctcacat    600
gttctttcct gcgttatccc ctgattctgt ggataaccgt attaccgcct ttgagtgagc    660
```

```
tgataccgct cgccgcagcc gaacgaccga gcgcagcgag tcagtgagcg aggaagcgga      720
agagcgccca atacgcaaac cgcctctccc cgcgcgttgg ccgattcatt aatgcagctg      780
gcacgacagg tttcccgact ggaaagcggg cagtgagcgc aacgcaatta atacgcgtac      840
cgctagccag gaagagtttg tagaaacgca aaaaggccat ccgtcaggat ggccttctgc      900
ttagtttgat gcctggcagt ttatggcggg cgtcctgccc gccacccctcc gggccgttgc     960 ttcacaacgt tcaaatccgc tcccggcgga tttgtcctac tcaggagagc gttcaccgac    1020
aaacaacaga taaaacgaaa ggcccagtct tccgactgag cctttcgttt tatttgatgc    1080
ctggcagttc cctactctcg cgttaacgct agcatggatg ttttcccagt cacgacgttg    1140
taaaacgacg ccagtctta agctcgggcc ccaaataatg attttatttt gactgatagt     1200
gacctgttcg ttgcaacaaa ttgatgagca atgcttttttt ataatgccaa ctttgtacaa   1260
aaaagcaggc tccgaattcg cccttccggg ctggtatatt aaaattacaa aaaaatttaa    1320
ataaaaaaat attaaaatat ttaatatatt ttaaacaata aaacattaaa ataaattaac    1380
aacatataaa ataaaaccat aaaaaatata catcatatta aataaaatta ttaataagta    1440
aaattaaaac tatttatttg aaaattaaat aaataatttt tttataattt gaaaaaatta    1500
gaaaaaaaac tgtaaaaaaa ataaaaacta ttattttttt aaaaacaaat aactttaaaa    1560
tttttttaaa aaaagtttta ctacttcaaa tcgtaagacc aacaaaaatt aaaaaaaatt    1620
acaactttga agttgtaaaa gaaaaaaaag ttgcttatga cttttaaaatt ataaaaaaaa   1680 taattaatat cataaataat tttatgattt taggtaaaaa aaaatacgaa gtcgtggtat    1740
cactactctt gactcaaaag ttgtgagaat ggttacaaat tattctcttt tcacgattat    1800
ttaaaaaaga cccagttgga aaaataaaaa aaaatatac ctaagcagta aaaaaaaacc     1860
ctaataatct ctagaaaaac ggaaagtaga tcgatcataa tccaataaaa agaggaaaaa    1920
agaaaacaaa agccgaaaga gaagagatac tgcggtaatt aaacaggtca gcaatgcaca    1980
caaaggtggc aattattaat tattaattaa taccagtaat tgaaagtgaa gaaaatgaaa    2040
aaacacacag acacacatgg gcaaaaaaga agtgtccagg ttcatcctcc tgaaccagtc    2100
tctgtcgaag aaggaaggcc ctttatatat aaaaacctaa actcgtattg ttctgagcaa    2160
cccaggttgt ctgttacgga ttagcatcaa agcaagttaa caaaatttgg gtgcgtcctg    2220
gattgaccct tttgccccct ctccctcacc ctccactaac tcctcctttt tggtttttat    2280
aaagcacatt cccaatagag gagggtccct acacaacaca acccttcaag ggcgaattcg    2340
acccagcttt cttgtacaaa gttggcatta taaaaaataa ttgctcatca atttgttgca    2400
acgaacaggt cactatcagt caaaataaaa tcattatttg ccatccagct gatatcccct    2460
atagtgagtc gtattacatg gtcatagctg tttcctggca gctctggccc gtgtctcaaa    2520
atctctgatg ttacattgca caagataaaa atatatcatc atgcctcctc tagaccagcc    2580
aggacagaaa tgcctcgact tcgctgctgc ccaaggttgc cgggtgacgc acaccgtgga    2640
aacggatgaa ggcacgaacc cagtggacat aagcctgttc ggttcgtaag ctgtaatgca    2700
agtagcgtat gcgctcacgc aactggtcca gaaccttgac cgaacgcagc ggtggtaacg    2760
gcgcagtggc ggttttcatg gcttgttatg actgtttttt tggggtacag tctatgcctc    2820
gggcatccaa gcagcaagcg cgttacgccg tgggtcgatg tttgatgtta tggagcagca    2880
acgatgttac gcagcagggc agtcgcccta aacaaagtt aaacatcatg agggaagcgg    2940
tgatcgccga agtatcgact caactatcag aggtagttgg cgtcatcgag cgccatctcg    3000
aaccgacgtt gctggccgta catttgtacg gctccgcagt ggatggcggc ctgaagccac    3060
```

```
acagtgatat tgatttgctg gttacggtga ccgtaaggct tgatgaaaca acgcggcgag    3120
ctttgatcaa cgaccttttg gaaacttcgg cttcccctgg agagagcgag attctccgcg    3180
ctgtagaagt caccattgtt gtgcacgacg acatcattcc gtggcgttat ccagctaagc    3240
gcgaactgca atttggagaa tggcagcgca atgacattct tgcaggtatc ttcgagccag    3300
ccacgatcga cattgatctg ctatcttgc tgacaaaagc aagagaacat agcgttgcct     3360
tggtaggtcc agcggcggag gaactctttg atccggttcc tgaacaggat ctatttgagg    3420
cgctaaatga aaccttaacg ctatggaact cgccgcccga ctgggctggc gatgagcgaa    3480
atgtagtgct tacgttgtcc cgcatttggt acagcgcagt aaccggcaaa atcgcgccga    3540
aggatgtcgc tgccgactgg gcaatggagc gcctgccggc ccagtatcag cccgtcatac    3600
ttgaagctag acaggcttat cttggacaag aagaagatcg cttggcctcg cgcgcagatc    3660
agttggaaga atttgtccac tacgtgaaag gcgagatcac caaggtagtc ggcaaataac    3720
cctcgagcca cccatgacca aaatcccttaa cgtgagtta cgcgtcgttc cactgagcgt    3780
cagaccccgt agaaaagatc aaaggatctt cttgagatcc ttttttttctg cgcgtaatct    3840 gctgcttgca aacaaaaaa                                                 3859

<210> SEQ ID NO 25
<211> LENGTH: 5286
<212> TYPE: DNA
<213> ORGANISM: Artificial sequence
<220> FEATURE:
<223> OTHER INFORMATION: plasmid QC330

<400> SEQUENCE: 25
cgcagatacc aaatactgtc cttctagtgt agccgtagtt aggccaccac ttcaagaact      60
ctgtagcacc gcctacatac ctcgctctgc taatcctgtt accagtggct gctgccagtg     120
gcgataagtc gtgtcttacc gggttggact caagacgata gttaccggat aaggcgcagc     180
ggtcgggctg aacggggggt tcgtgcacac agcccagctt ggagcgaacg acctacaccg     240
aactgagata cctacagcgt gagcattgag aaagcgccac gcttcccgaa gggagaaagg     300
cggacaggta tccggtaagc ggcagggtcg gaacaggaga gcgcacgagg gagcttccag     360
ggggaaacgc ctggtatctt tatagtcctg tcgggtttcg ccacctctga cttgagcgtc     420
gatttttgtg atgctcgtca ggggggcgga gcctatggaa aaacgccagc aacgcggcct     480
ttttacggtt cctggccttt tgctggcctt ttgctcacat gttctttcct gcgttatccc     540
ctgattctgt ggataaccgt attaccgcct ttgagtgagc tgataccgct cgccgcagcc     600
gaacgaccga gcgcagcgag tcagtgagcg aggaagcgga agagcgccca atacgcaaac     660
cgcctctccc cgcgcgttgg ccgattcatt aatgcaggtt gatcagatct cgatcccgcg     720
aaattaatac gactcactat agggagacca caacggtttc cctctagaaa taattttgtt     780
taactttaag aaggagatat acccatggaa aagcctgaac tcaccgcgac gtctgtcgag     840
aagtttctga tcgaaaagtt cgacagcgtc tccgacctga tgcagctctc ggagggcgaa     900
gaatctcgtg ctttcagctt cgatgtagga gggcgtggat atgtcctgcg ggtaaatagc     960
tgcgccgatg gtttctacaa agatcgttat gtttatcggc actttgcatc ggccgcgctc    1020
ccgattccgg aagtgcttga cattgggaa ttcagcgaga gcctgaccta ttgcatctcc     1080
cgccgtgcac agggtgtcac gttgcaagac ctgcctgaaa ccgaactgcc cgctgttctg    1140
cagccggtcg cggaggctat ggatgcgatc gctgcggccg atcttagcca gacgagcggg    1200
```

```
ttcggcccat tcggaccgca aggaatcggt caatacacta catggcgtga tttcatatgc    1260
gcgattgctg atccccatgt gtatcactgg caaactgtga tggacgacac cgtcagtgcg    1320
tccgtcgcgc aggctctcga tgagctgatg ctttgggccg aggactgccc cgaagtccgg    1380
cacctcgtgc acgcggattt cggctccaac aatgtcctga cggacaatgg ccgcataaca    1440
gcggtcattg actggagcga ggcgatgttc ggggattccc aatacgaggt cgccaacatc    1500
ttcttctgga ggccgtggtt ggcttgtatg gagcagcaga cgcgctactt cgagcggagg    1560
catccggagc ttgcaggatc gccgcggctc cgggcgtata tgctccgcat tggtcttgac    1620
caactctatc agagcttggt tgacggcaat ttcgatgatg cagcttgggc gcagggtcga    1680
tgcgacgcaa tcgtccgatc cggagccggg actgtcgggc gtacacaaat cgcccgcaga    1740
agcgcggccg tctggaccga tggctgtgta gaagtactcg ccgatagtgg aaaccgacgc    1800
cccagcactc gtccgagggc aaaggaatag tgaggtacag cttggatcga tccggctgct    1860
aacaaagccc gaaaggaagc tgagttggct gctgccaccg ctgagcaata actagcataa    1920 cccccttgggg cctctaaacg ggtcttgagg ggttttttgc tgaaaggagg aactatatcc    1980
ggatgatcgt cgaggcctca cgtgttaaca agcttgcatg cctgcaggtt tatcaacaag    2040
tttgtacaaa aaagctgaac gagaaacgta aaatgatata aatatcaata tattaaatta    2100
gattttgcat aaaaaacaga ctacataata ctgtaaaaca caacatatcc agtcatattg    2160
gcggccgcat taggcacccc aggctttaca ctttatgctt ccggctcgta taatgtgtgg    2220
attttgagtt aggatccgtc gagattttca ggagctaagg aagctaaaat ggagaaaaaa    2280
atcactggat ataccaccgt tgatatatcc caatggcatc gtaaagaaca ttttgaggca    2340
tttcagtcag ttgctcaatg tacctataac cagaccgttc agctggatat tacggccttt    2400
ttaaagaccg taaagaaaaa taagcacaag ttttatccgg cctttattca cattcttgcc    2460
cgcctgatga atgctcatcc ggaattccgt atggcaatga agacggtga gctggtgata    2520 tgggatagtg ttcacccttg ttacaccgtt ttccatgagc aaactgaaac gttttcatcg    2580
ctctggagtg aataccacga cgatttccgg cagtttctac acatatattc gcaagatgtg    2640
gcgtgttacg gtgaaaacct ggcctatttc cctaaagggt ttattgagaa tatgttttc    2700 gtctcagcca atccctgggt gagtttcacc agttttgatt taaacgtggc caatatggac    2760
aacttcttcg ccccgtttt caccatgggc aaatattata cgcaaggcga caaggtgctg    2820
atgccgctgg cgattcaggt tcatcatgcc gtttgtgatg cttccatgt cggcagaatg    2880 cttaatgaat acaacagta ctgcgatgag tggcagggcg gggcgtaaag atctggatcc    2940
ggcttactaa aagccagata acagtatgcg tatttgcgcg ctgattttg cggtataaga    3000 atatatactg atatgtatac ccgaagtatg tcaaaaagag gtatgctatg aagcagcgta    3060
ttacagtgac agttgacagc gacagctatc agttgctcaa ggcatatatg atgtcaatat    3120
ctccggtctg gtaagcacaa ccatgcagaa tgaagcccgt cgtctgcgtg ccgaacgctg    3180
gaaagcggaa aatcaggaag ggatggctga ggtcgcccgg tttattgaaa tgaacggctc    3240
ttttgctgac gagaacaggg gctggtgaaa tgcagtttaa ggtttacacc tataaaagag    3300
agagccgtta tcgtctgttt gtggatgtac agagtgatat tattgacacg cccgggcgac    3360
ggatggtgat ccccctggcc agtgcacgtc tgctgtcaga taaagtctcc cgtgaacttt    3420
acccggtggt gcatatcggg gatgaaagct ggcgcatgat gaccaccgat atggccagtg    3480
tgccggtctc cgttatcggg gaagaagtgg ctgatctcag ccaccgcgaa aatgacatca    3540
aaaacgccat taacctgatg ttctggggaa tataaatgtc aggctccctt atacacagcc    3600
```

```
agtctgcagg tcgaccatag tgactggata tgttgtgttt tacagtatta tgtagtctgt   3660
tttttatgca aaatctaatt taatatattg atatttatat cattttacgt ttctcgttca   3720
gctttcttgt acaaagtggt tgatgggatc catggcccac agcaagcacg gcctgaagga   3780
ggagatgacc atgaagtacc acatggaggg ctgcgtgaac ggccacaagt tcgtgatcac   3840
cggcgagggc atcggctacc ccttcaaggg caagcagacc atcaacctgt gcgtgatcga   3900
gggcggcccc ctgcccttca gcgaggacat cctgagcgcc ggcttcaagt acggcgaccg   3960
gatcttcacc gagtaccccc aggacatcgt ggactacttc aagaacagct gccccgccgg   4020
ctacacctgg ggccggagct tcctgttcga ggacggcgcc gtgtgcatct gtaacgtgga   4080
catcaccgtg agcgtgaagg agaactgcat ctaccacaag agcatcttca cggcgtgaa   4140 cttccccgcc gacggccccg tgatgaagaa gatgaccacc aactgggagg ccagctgcga   4200
gaagatcatg cccgtgccta agcagggcat cctgaagggc gacgtgagca tgtacctgct   4260
gctgaaggac ggcggccggt accggtgcca gttcgacacc gtgtacaagg ccaagagcgt   4320
gcccagcaag atgcccgagt ggcacttcat ccagcacaag ctgctgcggg aggaccggag   4380
cgacgccaag aaccagaagt ggcagctgac cgagcacgcc atcgccttcc ccagcgccct   4440
ggcctgagag ctcgaatttc cccgatcgtt caaacatttg gcaataaagt ttcttaagat   4500
tgaatcctgt tgccggtctt gcgatgatta tcatataatt tctgttgaat tacgttaagc   4560
atgtaataat taacatgtaa tgcatgacgt tatttatgag atgggttttt atgattagag   4620
tcccgcaatt atacatttaa tacgcgatag aaaacaaaat atagcgcgca aactaggata   4680
aattatcgcg cgcggtgtca tctatgttac tagatcggga attctagtgg ccggcccagc   4740
tgatatccat cacactggcg gccgctcgag ttctatagtg tcacctaaat cgtatgtgta   4800
tgatacataa ggttatgtat taattgtagc cgcgttctaa cgacaatatg tccatatggt   4860
gcactctcag tacaatctgc tctgatgccg catagttaag ccagccccga cacccgccaa   4920
cacccgctga cgcgccctga cgggcttgtc tgctcccggc atccgcttac agacaagctg   4980
tgaccgtctc cgggagctgc atgtgtcaga ggttttcacc gtcatcaccg aaacgcgcga   5040
gacgaaaggg cctcgtgata cgcctatttt tataggttaa tgtcatgacc aaaatccctt   5100
aacgtgagtt ttcgttccac tgagcgtcag accccgtaga aaagatcaaa ggatcttctt   5160
gagatccttt ttttctgcgc gtaatctgct gcttgcaaac aaaaaaacca ccgctaccag   5220
cggtggtttg tttgccggat caagagctac caactctttt tccgaaggta actggcttca   5280
gcagag                                                              5286
```

<210> SEQ ID NO 26
<211> LENGTH: 1867
<212> TYPE: DNA
<213> ORGANISM: Artificial sequence
<220> FEATURE:
<223> OTHER INFORMATION: plasmid QC398-1Y

<400> SEQUENCE: 26

```
ttgtacaaag tggttgatgg gatccatggc ccacagcaag cacggcctga aggaggagat     60
gaccatgaag taccacatgg agggctgcgt gaacggccac aagttcgtga tcaccggcga    120
gggcatcggc tacccccttca agggcaagca gaccatcaac ctgtgcgtga tcgagggcgg    180
ccccctgccc ttcagcgagg acatcctgag cgccggcttc aagtacgcgcg accggatctt    240 caccgagtac ccccaggaca tcgtggacta cttcaagaac agctgccccg ccggctacac    300
```

```
ctggggccgg agcttcctgt tcgaggacgg cgccgtgtgc atctgtaacg tggacatcac      360
cgtgagcgtg aaggagaact gcatctacca caagagcatc ttcaacgcgc tgaacttccc      420
cgccgacggc cccgtgatga agaagatgac caccaactgg gaggccagct gcgagaagat      480
catgcccgtg cctaagcagg gcatcctgaa gggcgacgtg agcatgtacc tgctgctgaa      540
ggacggcggc cggtaccggt gccagttcga caccgtgtac aaggccaaga gcgtgcccag      600
caagatgccc gagtggcact catccagca aagctgctg cgggaggacc ggagcgacgc        660
caagaaccag aagtggcagc tgaccgagca cgccatcgcc ttccccagcg ccctggcctg      720
agagctcgaa tttccccgat cgttcaaaca tttggcaata agtttcttta agattgaatc      780
ctgttgccgg tcttgcgatg attatcatat aatttctgtt gaattacgtt aagcatgtaa      840
taattaacat gtaatgcatg acgttattta tgagatgggt ttttatgatt agagtcccgc      900
aattatacat ttaatacgcg atagaaaaca aaatatagcg cgcaaactag gataaattat      960
cgcgcgcggt gtcatctatg ttactagatc gggaattcta gtggccggcc cagctgatat     1020
ccatcacact ggcggccgct cgagttctat agtgtcacct aaatcgtatg tgtatgatac     1080
ataaggttat gtattaattg tagccgcgtt ctaacgacaa tatgtccata tggtgcactc     1140
tcagtacaat ctgctctgat gccgcatagt taagccagcc ccgacacccg ccaacacccg     1200
ctgacgcgcc ctgacgggct tgtctgctcc cggcatccgc ttacagacaa gctgtgaccg     1260
tctccgggag ctgcatgtgt cagaggtttt caccgtcatc accgaaacgc gcgagacgaa     1320
agggcctcgt gatacgccta tttttatagg ttaatgtcat gaccaaaatc ccttaacgtg     1380
agttttcgtt ccactgagcg tcagaccccg tagaaaagat caaaggatct tcttgagatc     1440
cttttttttct gcgcgtaatc tgctgcttgc aaacaaaaaa accaccgcta ccagcggtgg     1500
tttgtttgcc ggatcaagag ctaccaactc tttttccgaa ggtaactggc ttcagcagag     1560
cgcagatacc aaatactgtc cttctagtgt agccgtagtt aggccaccac ttcaagaact     1620
ctgtagcacc gcctacatac ctcgctctgc taatcctgtt accagtggct gctgccagtg     1680
gcgataagtc gtgtcttacc gggttggact caagacgata gttaccggat aaggcgcagc     1740
ggtcgggctg aacggggggt tcgtgcacac agcccagctt ggagcgaacg acctacaccg     1800
aactgagata cctacagcgt gagcattgag aaagcgccac gcttcccgaa gggagaaagg     1860
cggacag                                                               1867
```

<210> SEQ ID NO 27
<211> LENGTH: 19
<212> TYPE: DNA
<213> ORGANISM: Artificial sequence
<220> FEATURE:
<223> OTHER INFORMATION: HPT forward primer (Hygro-57F)

<400> SEQUENCE: 27
cagcgtctcc gacctgatg                                                    19

<210> SEQ ID NO 28
<211> LENGTH: 16
<212> TYPE: DNA
<213> ORGANISM: Artificial sequence
<220> FEATURE:
<223> OTHER INFORMATION: FAM labeled HPT probe (Hygro-79T)

<400> SEQUENCE: 28
ctctcggagg gcgaag                                                       16

<210> SEQ ID NO 29
<211> LENGTH: 21
<212> TYPE: DNA
<213> ORGANISM: Artificial sequence
<220> FEATURE:
<223> OTHER INFORMATION: HPT reverse primer(Hygro-116R)

<400> SEQUENCE: 29
tcgaagctga aagcacgaga t                                         21

<210> SEQ ID NO 30
<211> LENGTH: 24
<212> TYPE: DNA
<213> ORGANISM: Artificial sequence
<220> FEATURE:
<223> OTHER INFORMATION: GFP forward primer(GFP-24F)

<400> SEQUENCE: 30
gaccaaggag atgaccatga agta                                      24

<210> SEQ ID NO 31
<211> LENGTH: 14
<212> TYPE: DNA
<213> ORGANISM: Artificial sequence
<220> FEATURE:
<223> OTHER INFORMATION: FAM labeled GFP probe (GFP-51T)

<400> SEQUENCE: 31
catggagggc tgcg                                                 14

<210> SEQ ID NO 32
<211> LENGTH: 20
<212> TYPE: DNA
<213> ORGANISM: Artificial sequence
<220> FEATURE:
<223> OTHER INFORMATION: GFP reverse primer (GFP-92R)

<400> SEQUENCE: 32
ccggtgatca cgaacttgtg                                           20

<210> SEQ ID NO 33
<211> LENGTH: 24
<212> TYPE: DNA
<213> ORGANISM: Artificial sequence
<220> FEATURE:
<223> OTHER INFORMATION: HSP forward primer (HSP-F1)

<400> SEQUENCE: 33
caaacttgac aaagccacaa ctct                                      24

<210> SEQ ID NO 34
<211> LENGTH: 20
<212> TYPE: DNA
<213> ORGANISM: Artificial sequence
<220> FEATURE:
<223> OTHER INFORMATION: VIC labeled HSP probe

<400> SEQUENCE: 34
ctctcatctc atataaatac                                           20

<210> SEQ ID NO 35
<211> LENGTH: 21
<212> TYPE: DNA
<213> ORGANISM: Artificial sequence
<220> FEATURE:
<223> OTHER INFORMATION: HSP reverse primer

```
<400> SEQUENCE: 35
ggagaaattg gtgtcgtgga a                                              21

<210> SEQ ID NO 36
<211> LENGTH: 100
<212> TYPE: DNA
<213> ORGANISM: Artificial sequence
<220> FEATURE:
<223> OTHER INFORMATION: attL1

<400> SEQUENCE: 36
caaataatga ttttattttg actgatagtg acctgttcgt tgcaacaaat tgataagcaa     60 tgcttttttta taatgccaac tttgtacaaa aaagcaggct                         100

<210> SEQ ID NO 37
<211> LENGTH: 100
<212> TYPE: DNA
<213> ORGANISM: Artificial sequence
<220> FEATURE:
<223> OTHER INFORMATION: attL2

<400> SEQUENCE: 37
caaataatga ttttattttg actgatagtg acctgttcgt tgcaacaaat tgataagcaa     60
tgctttctta taatgccaac tttgtacaag aaagctgggt                          100

<210> SEQ ID NO 38
<211> LENGTH: 125
<212> TYPE: DNA
<213> ORGANISM: Artificial sequence
<220> FEATURE:
<223> OTHER INFORMATION: attR1

<400> SEQUENCE: 38
acaagtttgt acaaaaaagc tgaacgagaa acgtaaaatg atataaatat caatatatta    60
aattagattt tgcataaaaa acagactaca taatactgta aaacacaaca tatccagtca   120
tattg                                                               125

<210> SEQ ID NO 39
<211> LENGTH: 125
<212> TYPE: DNA
<213> ORGANISM: Artificial sequence
<220> FEATURE:
<223> OTHER INFORMATION: attR2

<400> SEQUENCE: 39
accactttgt acaagaaagc tgaacgagaa acgtaaaatg atataaatat caatatatta    60
aattagattt tgcataaaaa acagactaca taatactgta aaacacaaca tatccagtca   120
ctatg                                                               125

<210> SEQ ID NO 40
<211> LENGTH: 21
<212> TYPE: DNA
<213> ORGANISM: Artificial sequence
<220> FEATURE:
<223> OTHER INFORMATION: attB1

<400> SEQUENCE: 40
caagtttgta caaaaaagca g                                              21

<210> SEQ ID NO 41
<211> LENGTH: 21
```

```
<212> TYPE: DNA
<213> ORGANISM: Artificial sequence
<220> FEATURE:
<223> OTHER INFORMATION: attB2

<400> SEQUENCE: 41
cagctttctt gtacaaagtg g                                             21

<210> SEQ ID NO 42
<211> LENGTH: 1664
<212> TYPE: DNA
<213> ORGANISM: Glycine max
<220> FEATURE:
<221> NAME/KEY: misc_feature
<222> LOCATION: (1)..(1664)
<223> OTHER INFORMATION: NCBI accession AF452454.2

<400> SEQUENCE: 42
ggcacgaggt ccatggccac tttcttcgcc caaacctcct tccccctccca ctctctctcc    60 aaaaccttcg atacccattt cgcccctgcc ccgaaagtca acgtctttgt gaacttcagg   120
gcgaggaggc acgttggggt gcgagtttcg aacgcgctga tcgaaccaga tggagggaag   180
ctcgtggagc ttgtggtgac ggattttgag agggatttga agaagggtga ggctcttttcg   240 ttgccgagga tcaagctctc aaggattgac cttgagtggg tccatgtcct cagcgaagga   300
tgggccacac ccctgaaagg cttcatgaga gaagccgagt tcctccaaac gcttcatttc   360
aactcgctcc gactcgatga tgggtcggtc gtgaacatgt cagtgcccat cgtgctggct   420
attgatgatg cgcagaagca tcggatcggg gataacaaaa aggttgctct ttttgattcc   480
aagggagacc ccgttgcaat tctcaataat attgagattt ataagcatcc taaagaagaa   540
agaatagccc gaacttgggg aaccattgcc cctggcctac cttatgttga acaaactata   600
accaatgctg gaaattggtt gattgggggt gacctagagg tcattgaacc aattcagtac   660
aatgatggac ttgatcattt tcgtctatct ccgacacaac tccgtgcaga gttcacaagg   720
cgcaatgcgg atgctgtgtt tgccttccag ctccggaatc ctgttcacaa tggccatgct   780
ttgctaatga ctgacacccg aaagcgcctt cttgagatgg gctataagaa tcctgtcctc   840
ttgcttcatc cacttggagg ctacaccaaa gctgatgatg tcccacttga ttggcgaatg   900
aagcaacatg agaaggtact tgaggatggt gttcttgatc cagagacaac tgtggtatcc   960
atattcccat ctcccatgca ctatgctgga cccacggagg tgcagtggca tgcaaaggct  1020
aggatcaatg caggggctaa cttctatatc gttggtcgtg accccgcagg catgagccat  1080
ccagttgaga aaagagatct gtatgatgct gaccatggaa agaaagtatt gagcatggca  1140
ccgggactag agcgtctaaa cattcttcct ttcagggttg ctgcatatga caagactcag  1200
ggtaaaatgg cattctttga cccttcaagg cctcaggact tcctgttcat atcaggcaca  1260
aagatgcgca cactggcaag gaacaaagaa agtcctcctg atggatttat gtgccctggt  1320
ggatggaagg tgctggttga ttactatgat agcttagtac tctcaagcaa cggcaaagtg  1380
caggaagctg ttccagctta atcttgtatc atatcataat gtatatatct catgattggg  1440
agaaacctta agcttatgta ttctcctgct aagacatact tcacgaggat cctctggccc  1500
aatctaataa taataataaa ttaaaacttt ggggaggcac aagcacggac acattgcctc  1560
tctctgtatg tatggcattt agacagcctc ttgcacttat ggtgcaattg tgcatgccaa  1620
ctctctgtaa tataatgtgg ttgtgctaag gatttgctcg tgcc                   1664

<210> SEQ ID NO 43
```

<211> LENGTH: 462
<212> TYPE: PRT
<213> ORGANISM: Glycine max

<400> SEQUENCE: 43

Met Ala Thr Phe Phe Ala Gln Thr Ser Phe Pro Ser His Ser Leu Ser
1               5                   10                  15

Lys Thr Phe Asp Thr His Phe Ala Pro Ala Pro Lys Val Asn Val Phe
            20                  25                  30

Val Asn Phe Arg Ala Arg Arg His Val Gly Val Arg Val Ser Asn Ala
        35                  40                  45

Leu Ile Glu Pro Asp Gly Gly Lys Leu Val Glu Leu Val Val Thr Asp
    50                  55                  60

Phe Glu Arg Asp Leu Lys Lys Gly Glu Ala Leu Ser Leu Pro Arg Ile
65                  70                  75                  80

Lys Leu Ser Arg Ile Asp Leu Glu Trp Val His Val Leu Ser Glu Gly
                85                  90                  95

Trp Ala Thr Pro Leu Lys Gly Phe Met Arg Glu Ala Glu Phe Leu Gln
            100                 105                 110

Thr Leu His Phe Asn Ser Leu Arg Leu Asp Asp Gly Ser Val Val Asn
        115                 120                 125

Met Ser Val Pro Ile Val Leu Ala Ile Asp Asp Ala Gln Lys His Arg
    130                 135                 140

Ile Gly Asp Asn Lys Lys Val Ala Leu Phe Asp Ser Lys Gly Asp Pro
145                 150                 155                 160

Val Ala Ile Leu Asn Asn Ile Glu Ile Tyr Lys His Pro Lys Glu Glu
                165                 170                 175

Arg Ile Ala Arg Thr Trp Gly Thr Ile Ala Pro Gly Leu Pro Tyr Val
            180                 185                 190

Glu Gln Thr Ile Thr Asn Ala Gly Asn Trp Leu Ile Gly Gly Asp Leu
        195                 200                 205

Glu Val Ile Glu Pro Ile Gln Tyr Asn Asp Gly Leu Asp His Phe Arg
    210                 215                 220

Leu Ser Pro Thr Gln Leu Arg Ala Glu Phe Thr Arg Arg Asn Ala Asp
225                 230                 235                 240

Ala Val Phe Ala Phe Gln Leu Arg Asn Pro Val His Asn Gly His Ala
                245                 250                 255

Leu Leu Met Thr Asp Thr Arg Lys Arg Leu Leu Glu Met Gly Tyr Lys
            260                 265                 270

Asn Pro Val Leu Leu Leu His Pro Leu Gly Gly Tyr Thr Lys Ala Asp
        275                 280                 285

Asp Val Pro Leu Asp Trp Arg Met Lys Gln His Glu Lys Val Leu Glu
    290                 295                 300

Asp Gly Val Leu Asp Pro Glu Thr Thr Val Val Ser Ile Phe Pro Ser
305                 310                 315                 320

Pro Met His Tyr Ala Gly Pro Thr Glu Val Gln Trp His Ala Lys Ala
                325                 330                 335

Arg Ile Asn Ala Gly Ala Asn Phe Tyr Ile Val Gly Arg Asp Pro Ala
            340                 345                 350

Gly Met Ser His Pro Val Glu Lys Arg Asp Leu Tyr Asp Ala Asp His
        355                 360                 365

Gly Lys Lys Val Leu Ser Met Ala Pro Gly Leu Glu Arg Leu Asn Ile
    370                 375                 380

Leu Pro Phe Arg Val Ala Ala Tyr Asp Lys Thr Gln Gly Lys Met Ala

-continued

```
            385                 390                 395                 400
Phe Phe Asp Pro Ser Arg Pro Gln Asp Phe Leu Phe Ile Ser Gly Thr
                405                 410                 415

Lys Met Arg Thr Leu Ala Arg Asn Lys Glu Ser Pro Pro Asp Gly Phe
                420                 425                 430

Met Cys Pro Gly Gly Trp Lys Val Leu Val Asp Tyr Asp Ser Leu
            435                 440                 445

Val Leu Ser Ser Asn Gly Lys Val Gln Glu Ala Val Pro Ala
        450                 455                 460
```

SOYBEAN ATPS PROMOTER AND ITS USE IN CONSTITUTIVE EXPRESSION OF TRANSGENIC GENES IN PLANTS

CROSS-REFERENCE TO RELATED APPLICATIONS

This application is a Divisional of U.S. application Ser. No. 14/344,326, filed Mar. 12, 2014, now U.S. Pat. No. 9,447,424 issued 20 Sep. 2016, which is a 371 of PCT Application No. PCT/US12/55170, filed Sep. 13, 2012 which claims the benefit of U.S. Patent Application No. 61/533,819, filed Sep. 13, 2011, all of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named 20160810_BB1914USDIV_SeqLst.txt created on Aug. 10, 2016 and having a size of 78 kilobytes and is filed concurrently with the specification. The sequence listing contained in this ASCII formatted document is part of the specification and is herein incorporated by reference in its entirety.

FIELD OF THE INVENTION

This invention relates to a plant promoter GM-ATPS and fragments thereof and their use in altering expression of at least one heterologous nucleotide sequence in plants in a tissue-independent or constitutive manner.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue—independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

SUMMARY OF THE INVENTION

This invention concerns an isolated polynucleotide comprising a promoter region of the ATPS *Glycine max* gene as set forth in SEQ ID NO:1, wherein said promoter comprises a deletion at the 5-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819 or 820 consecutive nucleotides, wherein the first nucleotide deleted is the cytosine nucleotide ['C'] at position 1 of SEQ ID NO:1. This invention also concerns the isolated polynucleotide of claim 1, wherein the polynucleotide is a constitutive promoter.

In a second embodiment, this invention concerns an isolated polynucleotide comprising a promoter wherein said promoter comprises the nucleotide sequence set forth in SEQ ID NOs: 1, 2, 3, 4, or 5 or said promoter comprises a functional fragment of the nucleotide sequence set forth in SEQ ID NOs: 1, 2, 3, 4, or 5.

In a third embodiment, this invention concerns a recombinant DNA construct comprising at least one heterologous nucleotide sequence operably linked to the promoter of the invention.

In a fourth embodiment, this invention concerns a cell, plant, or seed comprising a recombinant DNA construct of the present disclosure.

In a fifth embodiment, this invention concerns plants comprising this recombinant DNA construct and seeds obtained from such plants.

In a sixth embodiment, this invention concerns a method of altering (increasing or decreasing) expression of at least one heterologous nucleic acid fragment in a plant cell which comprises:

(a) transforming a plant cell with the recombinant expression construct described above;
(b) growing fertile mature plants from the transformed plant cell of step (a);
(c) selecting plants containing the transformed plant cell wherein the expression of the heterologous nucleic acid fragment is increased or decreased.

In a seventh embodiment, this invention concerns a method for expressing a green fluorescent protein ZS-GREEN1 in a host cell comprising:

(a) transforming a host cell with a recombinant expression construct comprising at least one ZS-GREEN1 (GFP) nucleic acid fragment operably linked to a promoter wherein said promoter consists essentially of the nucleotide sequence set forth in SEQ ID NOs:1, 2, 3, 4, or 5; and
(b) growing the transformed host cell under conditions that are suitable for expression of the recombinant DNA construct, wherein expression of the recombinant DNA construct results in production of increased levels of ZS-GREEN1 protein in the transformed host cell when compared to a corresponding nontransformed host cell.

In an eighth embodiment, this invention concerns an isolated nucleic acid fragment comprising a plant ATP sulfurylase (ATPS) gene promoter.

In an ninth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a tenth embodiment, this invention concerns an isolated polynucleotide linked to a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCE LISTINGS

The invention can be more fully understood from the following detailed description and the accompanying drawings and Sequence Listing that form a part of this application.

Figure 5:
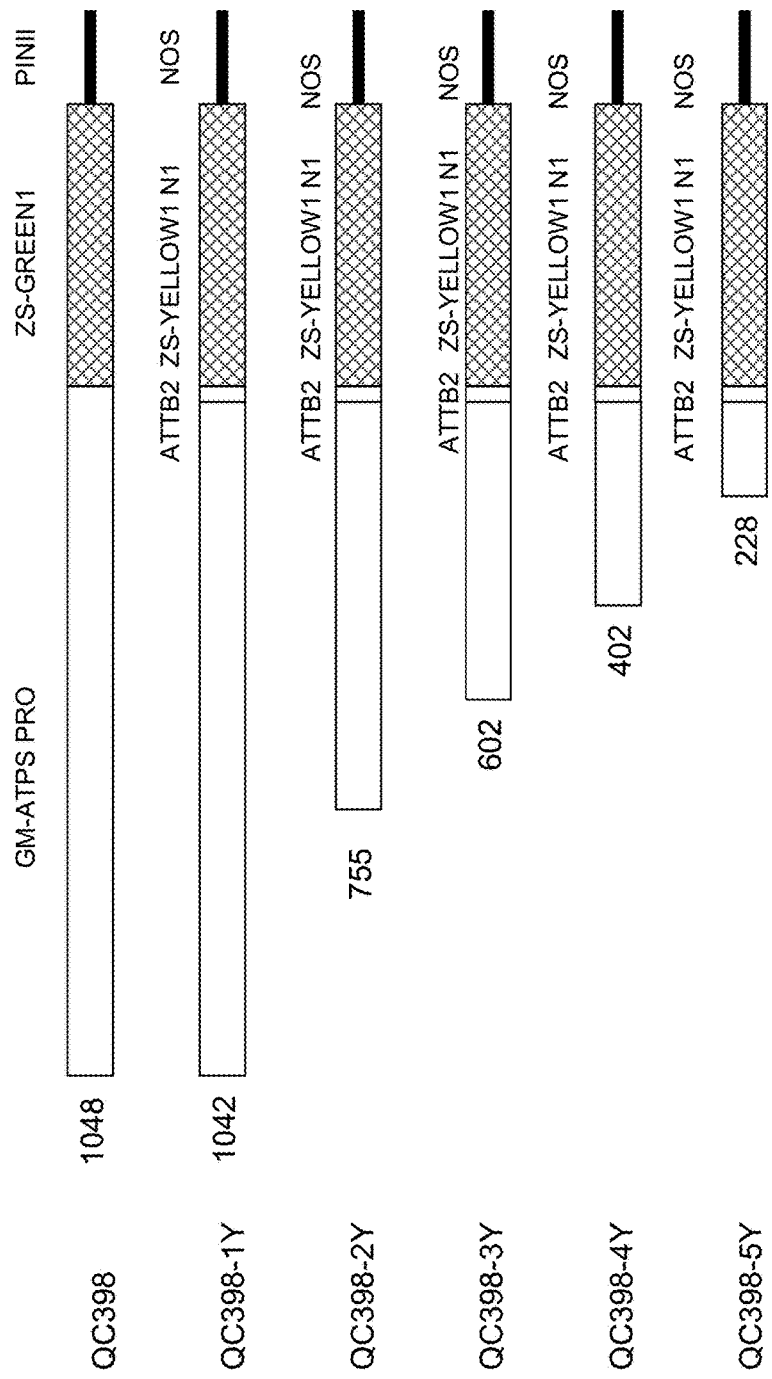

FIG. 5 is the schematic descriptions of the full length construct QC398 and its progressive truncation constructs, QC398-1Y, QC398-2Y, QC398-3Y, QC398-4Y, and QC398-5Y, of the ATPS promoter. The size of each promoter is given at the left end of each drawing. QC398-1Y has 1042 bp of the 1048 bp ATPS promoter in QC398 with the NcoI site removed and like the other deletion constructs with ZS-YELLOW N1 reporter gene.

Figure 6:
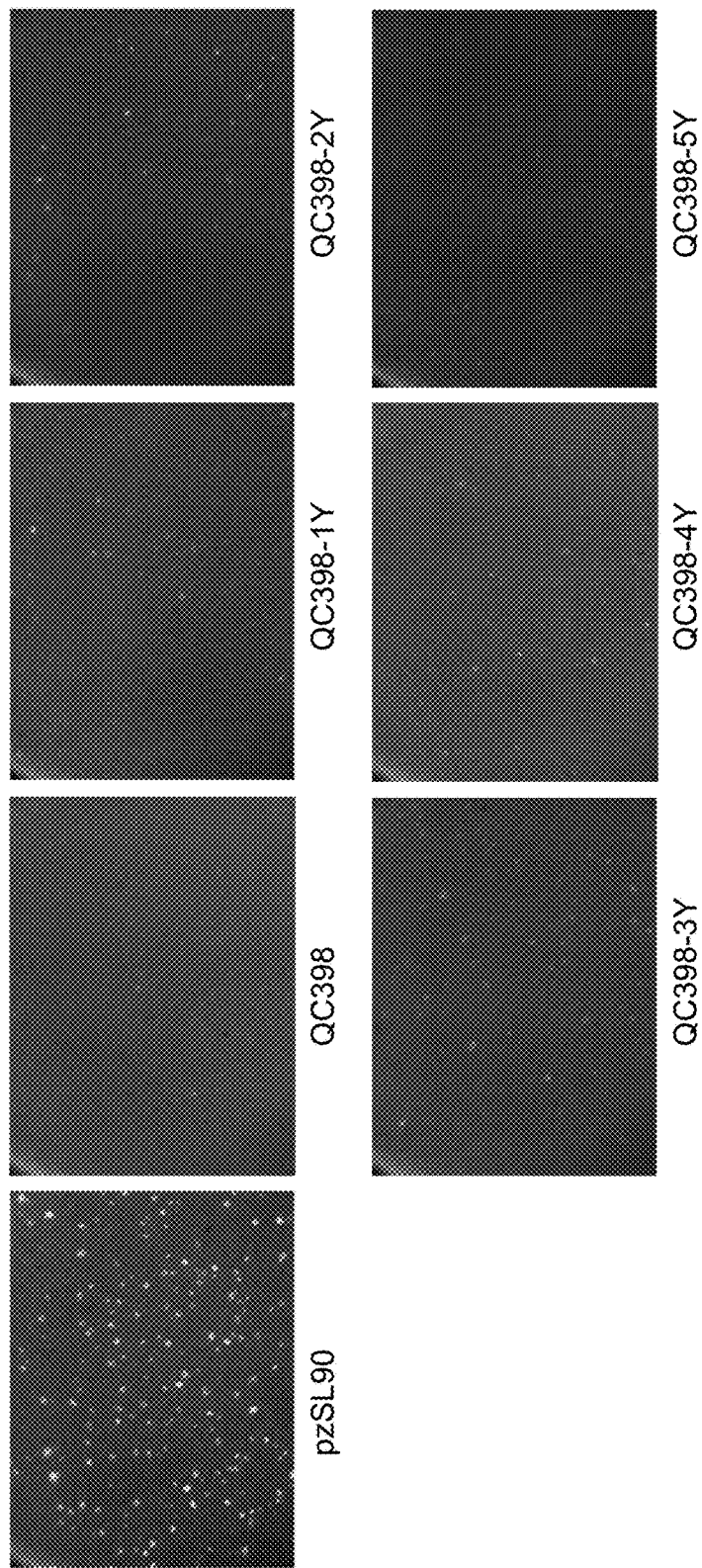

FIG. 6 is the transient expression of the fluorescent protein reporter gene ZS-YELLOW1 N1 in the cotyledons of germinating soybean seeds (shown as white spots). The reporter gene is driven by the full length ATPS promoter in QC398-1 or by progressively truncated ATPS promoters in the transient expression constructs QC398-2Y to QC398-5Y.

FIG. 7 A-P shows the stable expression of the fluorescent protein reporter gene ZS-GREEN1 in transgenic soybean plants containing a single copy of the transgene construct QC589. White areas (green in color display) indicate ZS-GREEN1 gene expression. Gray (red in color display) is background auto fluorescence from plant green tissues.

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2): 345-373 (1984).

SEQ ID NO:1 is the DNA sequence comprising a 1048 bp (base pair) soybean ATPS promoter.

SEQ ID NO:2 is a 755 bp truncated form of the ATPS promoter shown in SEQ ID NO:1 (bp 288-1042 of SEQ ID NO:1).

SEQ ID NO:3 is a 602 bp truncated form of the ATPS promoter shown in SEQ ID NO:1 (bp 441-1042 of SEQ ID NO:1).

SEQ ID NO:4 is a 402 bp truncated form of the ATPS promoter shown in SEQ ID NO:1 (bp 641-1042 of SEQ ID NO:1).

SEQ ID NO:5 is a 228 bp truncated form of the ATPS promoter shown in SEQ ID NO:1 (bp 815-1042 of SEQ ID NO:1).

SEQ ID NO:6 is an oligonucleotide primer used as a gene-specific antisense primer in the PCR amplification of the full length ATPS promoter in SEQ ID NO:1 when paired with SEQ ID NO:7.

SEQ ID NO:7 is an oligonucleotide primer used as a sense anchor primer in the PCR amplification of the full length ATPS promoter in SEQ ID NO:1 when paired with SEQ ID NO:6.

SEQ ID NO:8 is an oligonucleotide primer used as a gene-specific antisense primer in the PCR amplification of the full length ATPS promoter in SEQ ID NO:1 when paired with SEQ ID NO:9. A restriction enzyme NcoI recognition site CCATGG is introduced for convenient cloning.

SEQ ID NO:9 is an oligonucleotide primer used as a sense anchor primer in the PCR amplification of the full length ATPS promoter in SEQ ID NO:1 when paired with SEQ ID NO:8.

SEQ ID NO:10 is Clontech Universal GenomeWalker™ kit adaptor sequence.

SEQ ID NO:11 is an oligonucleotide primer used as an antisense primer in the PCR amplifications of the truncated ATPS promoters in SEQ ID NOs:1, 2, 3, 4, or 5 when paired with SEQ ID NOs: 12, 13, 14, 15, or 16, respectively.

SEQ ID NO:12 is an oligonucleotide primer used as a sense primer in the PCR amplification of the full length ATPS promoter in SEQ ID NO:1 when paired with SEQ ID NO:10.

SEQ ID NO:13 is an oligonucleotide primer used as a sense primer in the PCR amplification of the truncated ATPS promoter in SEQ ID NO:2 when paired with SEQ ID NO:10.

SEQ ID NO:14 is an oligonucleotide primer used as a sense primer in the PCR amplification of the truncated ATPS promoter in SEQ ID NO:3 when paired with SEQ ID NO:10.

SEQ ID NO:15 is an oligonucleotide primer used as a sense primer in the PCR amplification of the truncated ATPS promoter in SEQ ID NO:4 when paired with SEQ ID NO:10.

SEQ ID NO:16 is an oligonucleotide primer used as a sense primer in the PCR amplification of the truncated ATPS promoter in SEQ ID NO:5 when paired with SEQ ID NO:10.

SEQ ID NO:17 is the 1814 bp nucleotide sequence of the putative soybean ATP sulfurylase gene ATPS (PSO349758). Nucleotides 1 to 153 are the 5' untranslated sequence, nucleotides 154 to 156 are the translation initiation codon, nucleotides 154 to 1548 are the polypeptide coding region, nucleotides 1549 to 1551 are the termination codon, and nucleotides 1552 to 1814 are part of the 3' untranslated sequence.

SEQ ID NO:18 is the predicted 465 aa (amino acid) long peptide sequence translated from the coding region of the putative soybean ATP sulfurylase gene ATPS nucleotide sequence SEQ ID NO:16.

SEQ ID NO:19 is the 5208 bp sequence of plasmid QC274.

SEQ ID NO:20 is the 5298 bp sequence of plasmid QC397.

SEQ ID NO:21 is the 4391 bp sequence of plasmid QC398.

SEQ ID NO:22 is the 8406 bp sequence of plasmid QC586.

SEQ ID NO:23 is the 8913 bp sequence of plasmid QC589.

SEQ ID NO:24 is the 3859 bp sequence of plasmid QC398-1.

SEQ ID NO:25 is the 5286 bp sequence of plasmid QC330.

SEQ ID NO:26 is the 4700 bp sequence of plasmid QC398-1Y.

SEQ ID NO:27 is a sense primer used in quantitative PCR analysis of SCP1:HPT transgene copy numbers.

SEQ ID NO:28 is a FAM labeled fluorescent DNA oligo probe used in quantitative PCR analysis of SCP1:HPT transgene copy numbers.

SEQ ID NO:29 is an antisense primer used in quantitative PCR analysis of SCP1:HPT transgene copy numbers.

SEQ ID NO:30 is a sense primer used in quantitative PCR analysis of GM-ATPS:GFP transgene copy numbers.

SEQ ID NO:31 is a FAM labeled fluorescent DNA oligo probe used in quantitative PCR analysis of GM-ATPS:GFP transgene copy numbers.

SEQ ID NO:32 is an antisense primer used in quantitative PCR analysis of GM-ATP:GFP transgene copy numbers.

SEQ ID NO:33 is a sense primer used as an endogenous control gene primer in quantitative PCR analysis of transgene copy numbers.

SEQ ID NO:34 is a VIC labeled DNA oligo probe used as an endogenous control gene probe in quantitative PCR analysis of transgene copy numbers.

SEQ ID NO:35 is an antisense primer used as an endogenous control gene primer in quantitative PCR analysis of transgene copy numbers.

SEQ ID NO:36 is the recombination site attL1 sequence in the GATEWAY® cloning system (Invitrogen, Carlsbad, Calif.).

SEQ ID NO:37 is the recombination site attL2 sequence in the GATEWAY® cloning system (Invitrogen).

SEQ ID NO:38 is the recombination site attR1 sequence in the GATEWAY® cloning system (Invitrogen).

SEQ ID NO:39 is the recombination site attR2 sequence in the GATEWAY® cloning system (Invitrogen).

SEQ ID NO:40 is the recombination site attB1 sequence in the GATEWAY® cloning system (Invitrogen).

SEQ ID NO:41 is the recombination site attB2 sequence in the GATEWAY® cloning system (Invitrogen).

SEQ ID NO:42 is the nucleotide sequence of the *Glycine max* ATPS sulfurylase gene (NCBI Accession AF452454.2).

SEQ ID NO:43 is the amino acid sequence of the *Glycine max* ATPS sulfurylase gene (NCBI Accession AAL74418.2).

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, a "GM-ATPS promoter" refers to the promoter of a putative *Glycine max* gene with significant homology to ATP sulfurylase genes identified in various plant species including soybean that are deposited in National Center for Biotechnology Information (NCBI) database.

"Promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Constitutive promoter" refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

The promoter nucleotide sequences and methods disclosed herein are useful in regulating constitutive expression of any heterologous nucleotide sequences in a host plant in order to alter the phenotype of a plant.

A "heterologous nucleotide sequence" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The present invention encompasses functional fragments of the promoter sequences disclosed herein.

A "functional fragment" refer to a portion or subsequence of the promoter sequence of the present invention in which the ability to initiate transcription or drive gene expression (such as to produce a certain phenotype) is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the promoter of the present invention is any nucleic acid fragment that is capable of controlling the expression of a coding sequence or functional RNA in a similar manner to the promoter of the present invention.

In an embodiment of the present invention, the promoters disclosed herein can be modified. Those skilled in the art can create promoters that have variations in the polynucleotide sequence. The polynucleotide sequence of the promoters of the present invention as shown in SEQ ID NOS: 1-5, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present invention include, but are not limited to, combining control elements of different promoters or duplicating portions or regions of a promoter (see for example, U.S. Pat. No. 4,990,607; U.S. Pat. No. 5,110,732; and U.S. Pat. No. 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides of SEQ ID NO:1, SEQ ID NO:2, SEQ ID NO:3, SEQ ID NO:4 or SEQ ID NO:5. In another aspect of the present invention, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, of SEQ ID NO:1. In another aspect, a promoter fragment is the nucleotide sequence set forth in SEQ ID NO:2, SEQ ID NO:3, SEQ ID NO:4 or SEQ ID NO:5. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The isolated promoter sequence of the present invention can be modified to provide a range of constitutive expression levels of the heterologous nucleotide sequence. Thus, less than the entire promoter regions may be utilized and the ability to drive expression of the coding sequence retained.

However, it is recognized that expression levels of the mRNA may be decreased with deletions of portions of the promoter sequences. Likewise, the tissue-independent, constitutive nature of expression may be changed.

Modifications of the isolated promoter sequences of the present invention can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U. K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 97%, 98 and 99%.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.) or using the AlignX program of the Vector NTI bioinformatics computing suite (Invitrogen). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215: 403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Transient expression" refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paromomycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)- terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr. Opin. Cell Biol. 5, 242-246 (1993); Roberts et al. Annu. Rev. Plant Mol. Biol. 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode) or drought resistance, oil quantity and quality, or those increasing yield or nutritional quality may be employed as desired.

ATP sulfurylase (ATP:sulfate adenylyl transferase, EC 2.7.7.4) catalyzes the activation of sulfate by transferring sulfate to the adenine monophosphate moiety of ATP to form adenosine 5'-phosphosulfate (APS) and pyrophosphate (PPi). This enzyme participates in purine metabolism, selenoamino acid metabolism, and sulfur metabolism. It is the first enzyme of the sulfate assimilation pathway in plants and is present in chloroplast and cytosol as several different isoforms encoded by multiple genes. Though ATPS is constitutively expressed, it is most abundant in root tissue which can also be enhanced by cold treatment. Its transcript levels declines during seed development (Hatzfeld et al., Gene 248:51-58 (2000); Phartiyal et al., Arch. Biochem. Biophys. 450:20-29 (2006); Rotte and Leustek, Plant Physiol. 124: 715-724 (2000)). It is demonstrated herein that the soybean ATP sulfurylase gene promoter GM-ATPS can, in fact, be used as a constitutive promoter to drive expression of transgenes especially with preferred expression in root, and that such promoter can be isolated and used by one skilled in the art.

This invention concerns an isolated nucleic acid fragment comprising a constitutive metallothionein gene promoter ATPS. This invention also concerns an isolated nucleic acid fragment comprising a promoter wherein said promoter consists essentially of the nucleotide sequence set forth in SEQ ID NO:1, or an isolated polynucleotide comprising a promoter wherein said promoter comprises the nucleotide sequence set forth in SEQ ID NOs: 1, 2, 3, 4, or 5 or a functional fragment of SEQ ID NOs: 1, 2, 3, 4, or 5.

The expression patterns of ATPS gene and its promoter are set forth in Examples 1-7.

The promoter activity of the soybean genomic DNA fragment SEQ ID NO:1 upstream of the ATPS protein coding sequence was assessed by linking the fragment to a green fluorescence reporter gene, ZS-GREEN1 (GFP) (Tsien, Annu. Rev. Biochem. 67:509-544 (1998); Matz et al., Nat. Biotechnol. 17:969-973 (1999)), transforming the promoter:GFP expression cassette into soybean, and analyzing GFP expression in various cell types of the transgenic plants (see Example 6 and 7). GFP expression was detected in most parts of the transgenic plants though stronger expression was detected in roots and embryos. These results indicated that the nucleic acid fragment contained a constitutive promoter.

It is clear from the disclosure set forth herein that one of ordinary skill in the art could perform the following procedure:

1) operably linking the nucleic acid fragment containing the ATPS promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric ATPS promoter:reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sun-flower, safflower, cotton, tomato, potato, cocoa and the monocots, corn, wheat, rice, barley and palm.

3) testing for expression of the ATPS promoter in various cell types of transgenic plant tissues, e.g., leaves, roots, flowers, seeds, transformed with the chimeric ATPS promoter:reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention ATPS promoter or a fragment that is substantially similar and functionally equivalent to any portion of the nucleotide sequence set forth in SEQ ID NOs:1, 2, 3, 4, or 5 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to ATPS promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. No. 5,605,011, U.S. Pat. No. 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; 2$^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the ATPS promoter is weaker than that of many known strong promoters, such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis* oleosin promoters (Plant et al., Plant Mol. Biol. 25:193-205 (1994); Li, Texas A&M University Ph. D. dissertation, pp. 107-128 (1997)), the *Arabidopsis* ubiquitin extension protein promoters (Callis et al., J. Biol. Chem. 265(21):12486-

12493 (1990)), a tomato ubiquitin gene promoter (Rollfinke et al., Gene 211:267-276 (1998)), a soybean heat shock protein promoter, and a maize H3 histone gene promoter (Atanassova et al., Plant Mol. Biol. 37:275-285 (1998)). Universal weak expression of chimeric genes in most plant cells makes the ATPS promoter of the instant invention especially useful when low constitutive expression of a target heterologous nucleic acid fragment is required.

Another general application of the ATPS promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the ATPS promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the ATPS promoter of the present invention. (See U.S. Pat. No. 5,107, 065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:

(a) transforming a plant cell with the recombinant expression construct described herein;
(b) growing fertile mature plants from the transformed plant cell of step (a);
(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

Non-limiting examples of methods and compositions disclosed herein are as follows:

1. An isolated polynucleotide comprising a promoter region of the ATPS *Glycine max* gene as set forth in SEQ ID NO:1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819 or 820 consecutive nucleotides, wherein the first nucleotide deleted is the cytosine nucleotide ['C'] at position 1 of SEQ ID NO:1.

2. The isolated polynucleotide of embodiment 1, wherein the polynucleotide is a constitutive promoter.

3. An isolated polynucleotide comprising:
(a) a nucleotide sequence comprising the sequence set forth in SEQ ID NO:1, SEQ ID NO:2, SEQ ID NO:3, SEQ ID NO:4, or SEQ ID NO:5, or a functional fragment thereof; or,
(b) a full-length complement of (a); or,
(c) a nucleotide sequence comprising a sequence having at least 90% sequence identity, based on the BLASTN method of alignment, when compared to the nucleotide sequence of (a);
wherein said nucleotide sequence is a promoter.

4. The isolated polynucleotide of embodiment 3, wherein the nucleotide sequence of (b) has at least 95% identity, based on the BLASTN method of alignment, when compared to the sequence set forth in SEQ ID NO:1.
  5. The isolated polynucleotide of embodiment 3, wherein the polynucleotide is a constitutive promoter.
  6. A recombinant DNA construct comprising the isolated polynucleotide of any one of embodiments 1-5 operably linked to at least one heterologous nucleotide sequence.
  7. A vector comprising the recombinant DNA construct of embodiment 6.
  8. A cell comprising the recombinant DNA construct of embodiment 6.
  9. The cell of embodiment 8, wherein the cell is a plant cell.
  10. A transgenic plant having stably incorporated into its genome the recombinant DNA construct of embodiment 6.
  11. The transgenic plant of embodiment 10 wherein said plant is a dicot plant.
  12. The transgenic plant of embodiment 11 wherein the plant is soybean.
  13. A transgenic seed produced by the transgenic plant of embodiment 10.
  14. The recombinant DNA construct according to embodiment 6, wherein the at least one heterologous nucleotide sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.
  15. The recombinant DNA construct according to embodiment 6, wherein the at least one heterologous nucleotide sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.
  16. A method of expressing a coding sequence or a functional RNA in a plant comprising:
    a) introducing the recombinant DNA construct of embodiment 6 into the plant, wherein the at least one heterologous nucleotide sequence comprises a coding sequence or a functional RNA;
    b) growing the plant of step a); and
    c) selecting a plant displaying expression of the coding sequence or the functional RNA of the recombinant DNA construct.
  17. A method of transgenically altering a marketable plant trait, comprising:
    a) introducing a recombinant DNA construct of embodiment 6 into the plant;
    b) growing a fertile, mature plant resulting from step a); and
    c) selecting a plant expressing the at least one heterologous nucleotide sequence in at least one plant tissue based on the altered marketable trait.
  18. The method of embodiment 17 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.
  19. A method for altering expression of at least one heterologous nucleic acid fragment in plant comprising:
    (a) transforming a plant cell with the recombinant DNA construct of embodiment 6;
    (b) growing fertile mature plants from transformed plant cell of step (a); and
    (c) selecting plants containing the transformed plant cell wherein the expression of the heterologous nucleic acid fragment is increased or decreased.
  20. The method of Embodiment 19 wherein the plant is a soybean plant.
  21. A method for expressing a yellow fluorescent protein ZS-GREEN1 in a host cell comprising:
    (a) transforming a host cell with the recombinant DNA construct of embodiment 6; and,
    (b) growing the transformed host cell under conditions that are suitable for expression of the recombinant DNA construct, wherein expression of the recombinant DNA construct results in production of increased levels of ZS-GREEN1 protein in the transformed host cell when compared to a corresponding non-transformed host cell.
  22. A plant stably transformed with a recombinant DNA construct comprising a soybean constitutive promoter and a heterologous nucleic acid fragment operably linked to said constitutive promoter, wherein said constitutive promoter is a capable of controlling expression of said heterologous nucleic acid fragment in a plant cell, and further wherein said constitutive promoter comprises a fragment of SEQ ID NO:1.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Constitutive Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene were compiled electronically based on their overlapping sequence homology into a unique full length sequence representing the gene. These assembled unique gene sequences were accumulatively collected in Pioneer Hi-Bred Intl proprietary searchable databases.

To identify constitutive promoter candidate genes, searches were performed to look for gene sequences that were found at similar frequencies in leaf, root, flower, embryos, pod, and also in other tissues. One unique gene PSO349758 was identified in the search to be a weak constitutive gene candidate. PSO349758 cDNA sequence (SEQ ID NO:17) as well as its putative translated protein sequence (SEQ ID NO:18) were used to search National Center for Biotechnology Information (NCBI) databases. Both PSO349758 nucleotide and amino acid sequences were found to have high homology to ATP sulfurylase genes discovered in several plant species including identical soybean cDNA (NCBI accession AF452454.2; SEQ ID NO:42) and protein (NCBI accession AAL74418.2; SEQ ID NO:43) sequences.

Solexa digital gene expression dual-tag-based mRNA profiling using the Illumina (Genome Analyzer) GA2 machine is a restriction enzyme site anchored tag-based technology, in this regard similar to Mass Parallel Signature Sequence transcript profiling technique (MPSS), but with two key differences (Morrissy et al., Genome Res. 19:1825-1835 (2009); Brenner et al., Proc. Natl. Acad. Sci. USA 97:1665-70 (2000)). Firstly, not one but two restriction enzymes were used, DpnII and NlaI, the combination of which increases gene representation and helps moderate expression variances. The aggregate occurrences of all the resulting sequence reads emanating from these DpnII and NlaI sites, with some repetitive tags removed computationally, were used to determine the overall gene expression levels. Secondly, the tag read length used here is 21 nucleotides, giving the Solexa tag data higher gene match fidelity than the shorter 17-mers used in MPSS. Soybean mRNA global gene expression profiles are stored in a Pioneer proprietary database TDExpress (Tissue Development Expression Browser). Candidate genes with different expression patterns can be searched, retrieved, and further evaluated.

Figure 1:
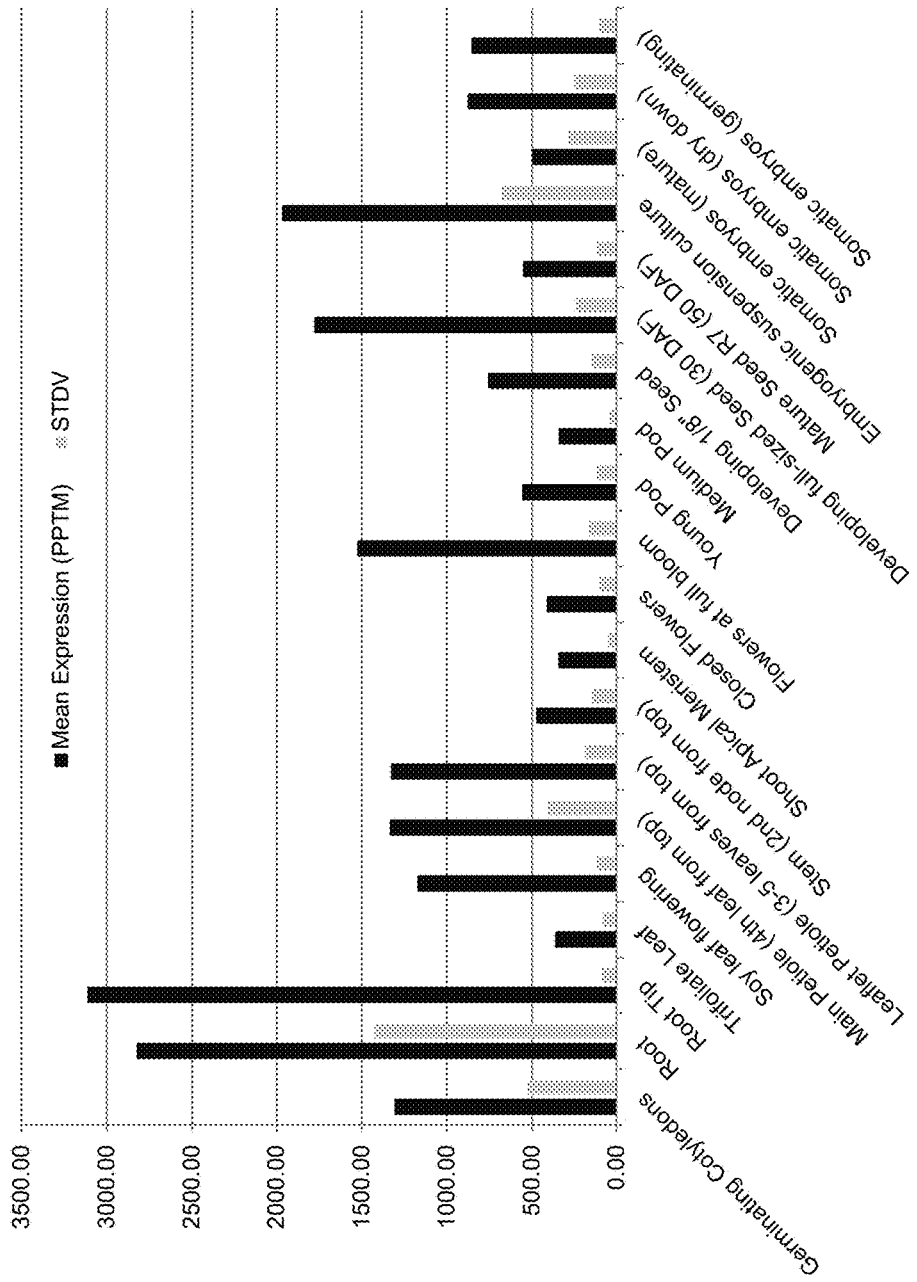
FIG. 1 is the relative expression of the soybean ATP sulfurylase (ATPS) gene (Glyma10g38760.1) in twenty soybean tissues by Illumina (Solexa) digital gene expression dual-tag-based mRNA profiling. The gene expression profile indicates that the ATPS gene is expressed in all the checked tissues.

The ATP sulfurylase gene PSO349758 corresponds to predicted gene Glyma10g38760.1 in the soybean genome, sequenced by the DOE-JGI Community Sequencing Program consortium (Schmutz J, et al., Nature 463:178-183 (2010)). The ATPS expression profiles in twenty tissues were retrieved from the TDExpress database using the gene ID Glyma10g38760.1 and presented as parts per ten millions (PPTM) averages of three experimental repeats (FIG. 1). The ATPS gene is expressed in all checked tissues at relative low levels with the highest expression detected in root and root tip, which is consistent with its EST profiles as a weakly expressed constitutive gene with preferred expression in root.

Example 2

Isolation of Soybean ATPS Promoter

The soybean genomic DNA fragment corresponding to the ATPS promoter of PSO349758 was isolated using a polymerase chain reaction (PCR) based approach called genome walking using the Universal GenomeWalker™ kit from Clontech™ (Product User Manual No. PT3042-1). Soybean genomic DNA was digested to completion with a DNA restriction enzyme that generates blunt ends (DraI, EcoRV, HpaI or PmlI, for example) according to standard protocols. Double strand adaptors supplied in the GenomeWalker kit were added to the blunt ends of the genomic DNA fragments by DNA ligase. Two rounds of PCR were performed to amplify the ATPS corresponding genomic DNA fragment using two nested primers supplied in the Universal GenomeWalker™ kit that are specific for the adaptor sequence (AP1 and AP2, for the first and second adaptor primer, respectively), and two ATPS gene PSO349758 specific primers (PSO349758-A1 and PSO349758-A2) designed based on the PSO349758 5' coding sequence. The oligonucleotide sequences of the four primers are shown below:

```
SEQ ID NO: 6 (PSO349758-A1):
AGGTTTGGGCGAAGAAAGTGGC

SEQ ID NO: 7 (AP1):
GTAATACGACTCACTATAGGGCACG

SEQ ID NO: 8 (PSO349758-A2):
CCATGGAAGGGTTGTGTTGTGTAGGGACCC

SEQ ID NO: 9 (AP2):
CTATAGGGCACGCGTGGTCGAC
```

The underlined bases in PSO349758-A2 primer are the recognition site for the restriction enzyme NcoI. The AP2 primer from the Universal GenomeWalker™ kit contains a SalI restriction site. The 3' end of the adaptor sequence SEQ ID NO:10 GTAATACGACTCACTATAGGGCACGCGTGGTCGACGGCCCGGGCTGGT also contains a XmaI recognition site downstream to the corresponding SalI recognition site in AP2 primer.

The AP1 and the PSO349758-A1 primers were used in the first round PCR using each of the adaptor ligated genomic DNA populations (DraI, EcoRV, HpaI or PmlI) under conditions defined in the GenomeWalker™ protocol. Cycle conditions were 94° C. for 4 minutes; 35 cycles of 94° C. for 30 seconds, 60° C. for 1 minute, and 68° C. for 3 minutes; and a final 68° C. for 5 minutes before holding at 4° C.

Figure 3A:
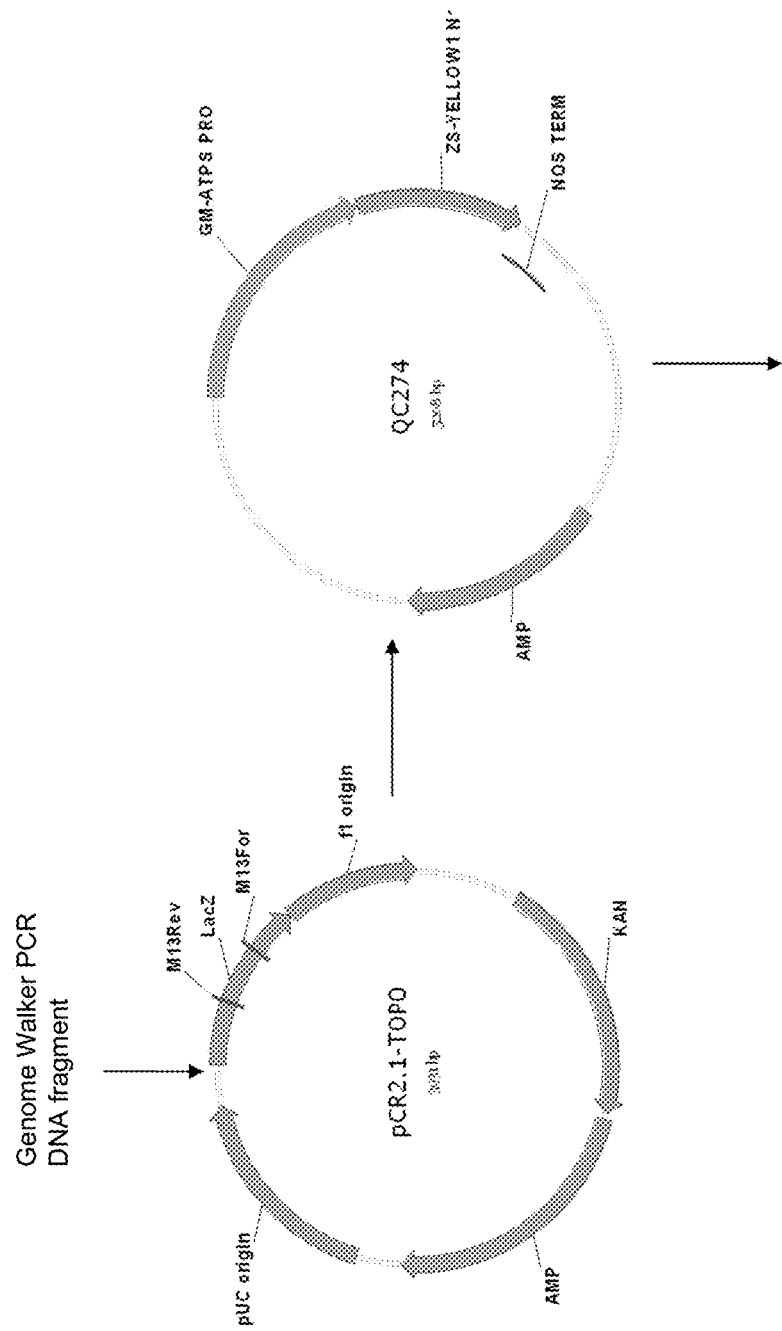
FIG. 3A-3C shows the maps of plasmid pCR2.1-TOPO, QC274, QC397, QC398, QC586, and QC589.
Figure 3:
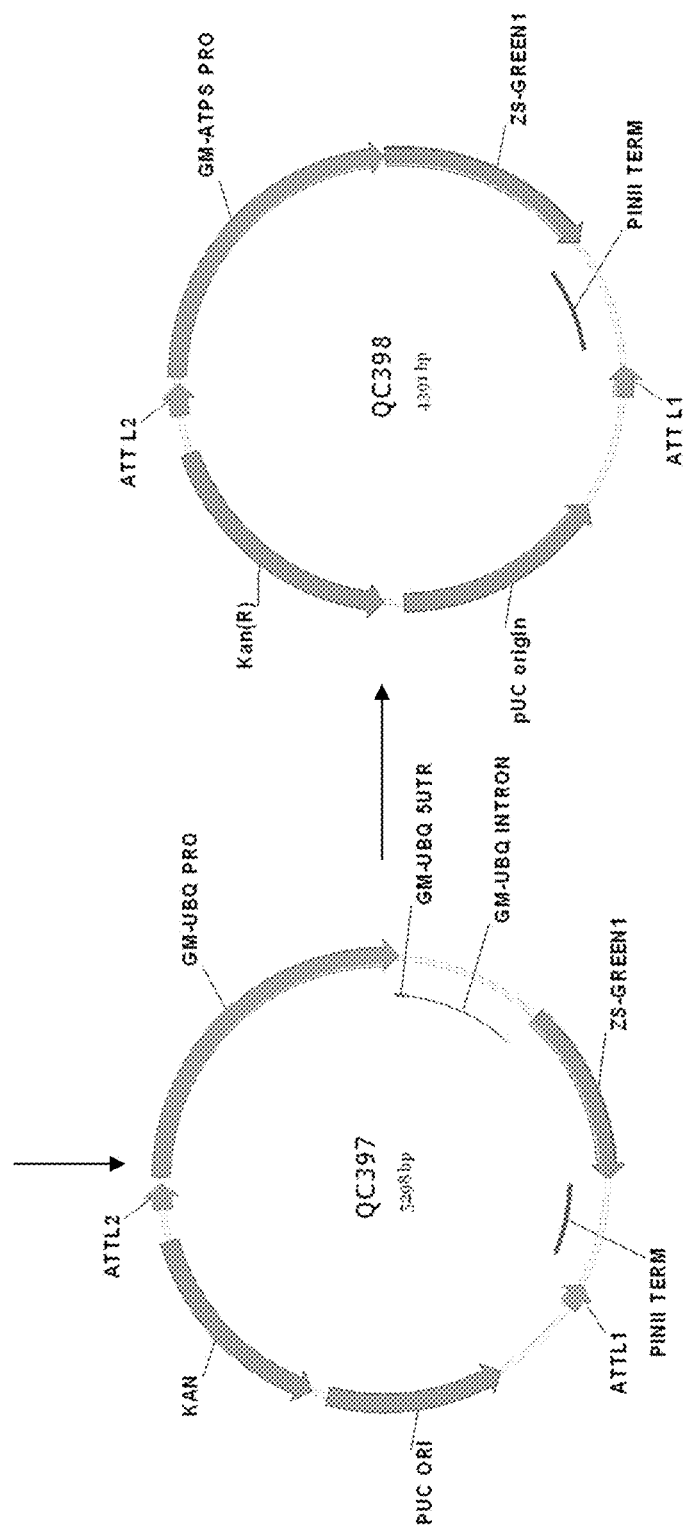

One microliter from each of the first round PCR products was used as templates for the second round PCR with the AP2 and PSO349758-A2 primers. Cycle conditions were 94° C. for 4 minutes; 25 cycles of 94° C. for 30 seconds, 60° C. for 1 minute, and 68° C. for 3 minutes; and a final 68° C. for 5 minutes before holding at 4° C. Agarose gels were run to identify specific PCR product with an optimal fragment length. An approximately 1.1 Kb PCR product was detected and subsequently cloned into pCR2.1-TOPO vector by TOPO TA cloning (Invitrogen) (FIG. 3A). Sequencing of the cloned PCR product revealed that its 3' end matched perfectly to the 5' end of the PSO349758 ATPS cDNA sequence, indicating that the PCR product was indeed the corresponding ATPS genomic DNA fragment. The 1048 bp sequence upstream of the putative ATPS start codon ATG including the XmaI and NcoI sites is herein designated as soybean ATPS promoter SEQ ID NO:1.

Example 3

ATPS Promoter Copy Number Analysis

Figure 2:
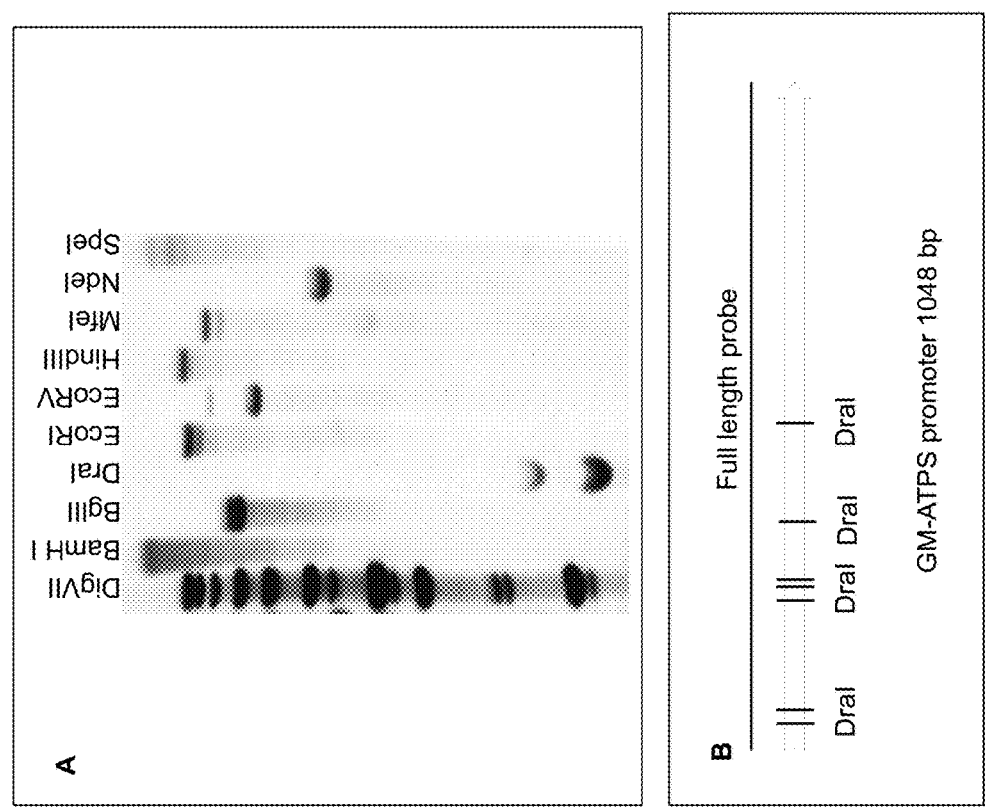
FIG. 2 is ATPS promoter copy number analysis by Southern.

Southern hybridization analysis was performed to examine whether additional copies or sequences with significant similarity to the ATPS promoter exist in the soybean genome. Soybean 'Jack' wild type genomic DNA was digested with nine different restriction enzymes, BamHI, BglII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled ATPS promoter DNA probe in Easy-Hyb Southern hybridization solution, and then sequentially washed 10 minutes with 2×SSC/0.1% SDS at room temperature and 3×10 minutes at 65° C. with 0.1× SSC/0.1% SDS according to the protocol provided by the manufacturer (Roche Applied Science, Indianapolis, Ind.). The ATPS promoter probe was labeled by PCR using the DIG DNA labeling kit (Roche Applied Science) with primers AP2 (SEQ ID NO:9) and PSO349758-A2 (SEQ ID NO:8) and QC274 DNA (SEQ ID NO:19, FIG. 3A) as the template to make a 1072 bp long probe covering the full length ATPS promoter (FIG. 2B).

Only DraI of the nine restriction enzymes could cut the 1048 bp ATPS promoter sequence and it would cut seven times all in the 5' half making the fragments too small to be detected by Southern hybridization. Only the 3' end 525 bp half was long enough to hybridize to the probe so only one band for each copy of ATPS would be expected with DraI digestion. None of the other eight restriction enzymes BamHI, BglII, EcoRI, EcoRV, HindIII, MfeI, NdeI, and SpeI would cut the promoter. Therefore, only one band would be expected to be hybridized for each of the eight digestions if only one copy of ATPS sequence exists in soybean genome (FIG. 2B). The observation that one major band was detected in all the nine digestions suggested that there is only one copy of ATPS promoter sequence (SEQ ID NO:1) in soybean genome (FIG. 2A). Meanwhile, one minor band was clearly detected in DraI and EcoRV digestions, and two minor bands were detected in EcoRI, MfeI, and SpeI digestions, suggesting that there is a different sequence with high similarity to the ATPS promoter in soybean genome. The DIGVII molecular markers used on the Southern blot are 8576, 7427, 6106, 4899, 3639, 2799, 1953, 1882, 1515, 1482, 1164, 992, 718, 710 bp. Some non-specific bands were hybridized and some smaller bands were cut off.

Since the whole soybean genome sequence is now publically available (Schmutz J, et al., Nature 463:178-183 (2010)), the ATPS promoter copy numbers can also be evaluated by searching the soybean genome with the 1048 bp promoter sequence. Consistent with above Southern analysis, only one identical sequence Gm10:46532420-46531389 complementarily matching the ATPS promoter sequence 12-1043 is identified. The first 11 bp ATPS promoter sequence <u>CCCGGGCTGGT</u> is non soybean sequence derived from the Clontech Universal GenomeWalker™ adaptor SEQ ID NO:10. The 5' half 12-540 bp of the ATPS promoter sequence also matches complementarily to a similar sequence Gm12:33505688-33505152 with a score of 441.3 bits, an E-value of 9.0e-122, and 78.8% identity. The 3' half 685-1043 bp of the ATPS promoter sequence also matches a similar sequence Gm20:37939304-37939626 with a score of 369.2 bits, an E-value of 7.2e-100, and 82.5% identify. The two similar sequences may correspond to the minor Southern bands (FIG. 2A).

Example 4

ATPS:GFP Reporter Gene Constructs and Soybean Transformation

The ATPS promoter in GATEWAY® entry construct (Invitrogen) described in EXAMPLE 3 was cloned as a PstI-NcoI fragment upstream of the fluorescent reporter gene ZS-YELLOW1 N1 to make the ATPS:YFP expression cassette QC274 (SEQ ID NO:19) (FIG. 3A). The same ATPS promoter was then cloned as an XmaI-NcoI fragment upstream of the ZS-GREEN1 fluorescent reporter gene of QC397 (SEQ ID NO:20) to make the ATPS:GFP expression cassette QC398 (SEQ ID NO:21) as a GATEWAY® entry construct (FIG. 3B). The ATPS:GFP cassette was moved into a GATEWAY® destination vector QC586 (SEQ ID NO:22) by LR Clonase® (Invitrogen) mediated DNA recombination between the attL1 and attL2 recombination sites (SEQ ID NO:36, and 37, respectively) in QC398 and the attR1-attR2 recombination sites (SEQ ID NO:38, and 39, respectively) in QC586 to make the final transformation construct QC589 (SEQ ID NO:23) (FIG. 3C).

Figure 3C:
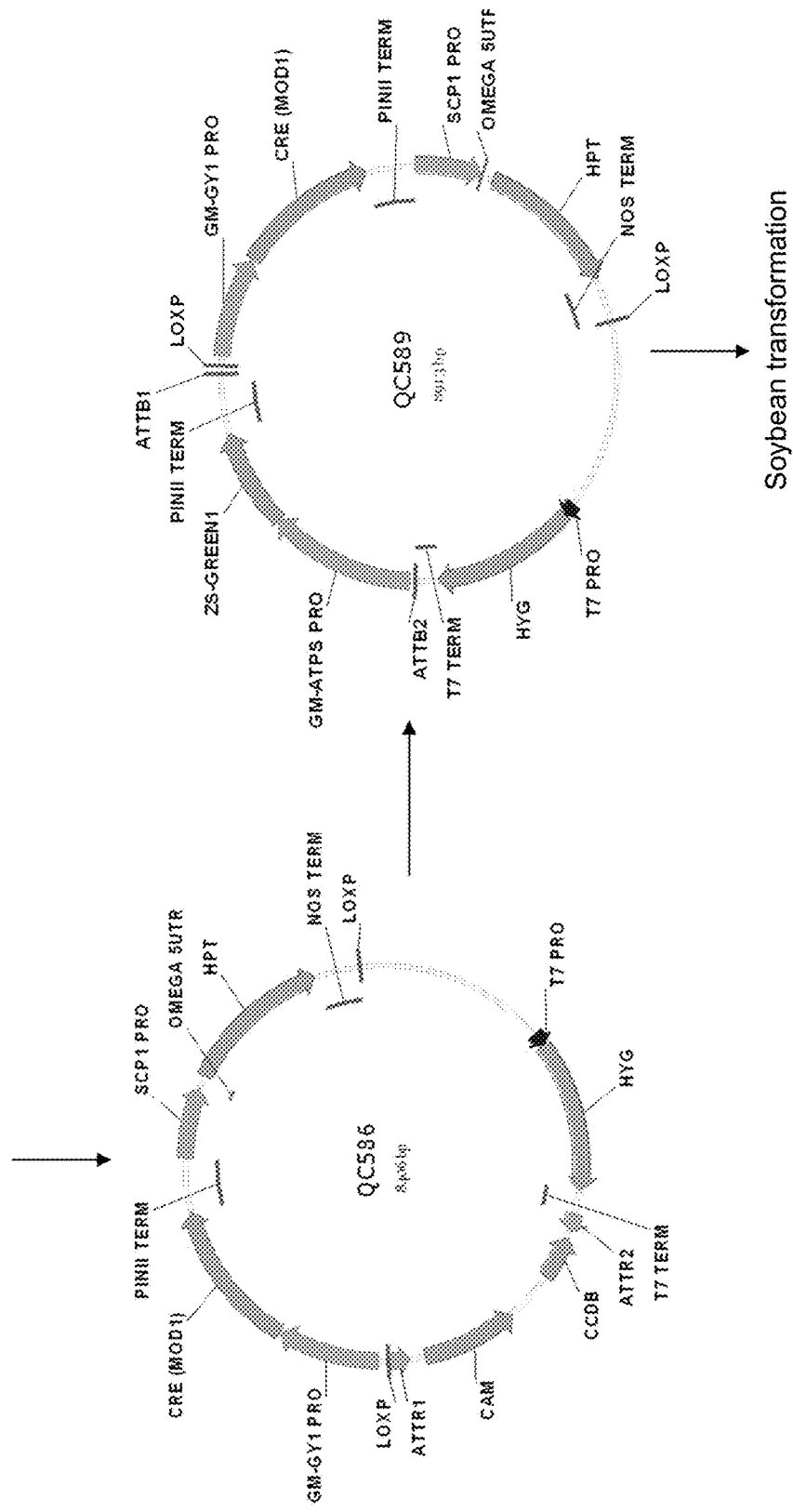

Since the destination vector QC586 already contains a soybean transformation selectable marker gene SCP1:HPT, the resulting DNA construct QC589 has the ATPS:GFP gene expression cassette linked to the GY1:CRE and SCP1:HPT cassettes (FIG. 3C). The GY1:CRE cassette can express CRE recombinase during the late stage of transformation to activate gene excision to remove the GY1:CRE and SCP1:HPT cassettes flanked by the LoxP sites from the final transgenic plants. Two 21 bp recombination sites attB1 and attB2 (SEQ ID NO:40, and 41, respectively) were newly created recombination sites resulting from DNA recombination between attL1 and attR1, and between attL2 and attR2, respectively. The 6399 bp DNA fragment containing the linked ATPS:GFP, GY1:CRE, and SCP1:HPT expression cassettes was isolated from plasmid QC589 (SEQ ID NO:23) with AscI digestion (positions 6699-4184), separated from the vector backbone fragment by agarose gel electrophoresis, and purified from the gel with a DNA gel extraction kit (QIAGEN®, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the ATPS promoter activity in stably transformed soybean plants.

The same methodology as outlined above for the ATPS:YFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/µl QC589 DNA fragment ATPS:GFP+GY1:CRE+SCP1:HPT, 20 µl of 0.1 M spermidine, and 25 µl of 5 M $CaCl_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. 5 µl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 µg/ml hygromycin B as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA were extracted from somatic embryo samples and analyzed by quantitative PCR using the 7500 real time PCR system (Applied Biosystems) with gene-specific primers and FAM-labeled fluorescence probes to check copy numbers of both the SCP1:HPT expression cassette and the ATPS:GFP expression cassette. The qPCR analysis was done in duplex reactions with a heat shock protein (HSP) gene as the endogenous controls and a transgenic DNA sample with a known single copy of HPT or GFP transgene as the calibrator using the relative quantification methodology (Applied Biosystems). The endogenous control HSP probe was labeled with VIC and the target gene HPT or GFP probe was labeled with FAM for the simultaneous detection of both fluorescent probes (Applied Biosystems).

The primers and probes used in the qPCR analysis are listed below.
HPT forward primer: SEQ ID NO:27
FAM labeled HPT probe: SEQ ID NO:28
HPT reverse primer: SEQ ID NO:29
GFP forward primer: SEQ ID NO:30
FAM labeled GFP probe: SEQ ID NO:31
GFP reverse primer: SEQ ID NO:32
HSP forward primer: SEQ ID NO:33
VIC labeled HSP probe: SEQ ID NO:34
HSP reverse primer: SEQ ID NO:35

Only transgenic soybean events containing 1 or 2 copies of both the SCP1:HPT expression cassette and the ATPS:GFP expression cassette were selected for further gene expression evaluation and seed production (see Table 1). Events negative for GFP qPCR or with more than 2 copies for the HPT qPCR were not further followed. GFP expressions are described in detail in EXAMPLE 7 and are also summarized in Table 1.

TABLE 1

Relative transgene copy numbers and GFP expression of ATPS:GFP transgenic plants

| Clone ID | GFP expression | GFP qPCR | HPT qPCR |
| --- | --- | --- | --- |
| 6634.1.2 | + | 1.3 | 0.8 |
| 6634.1.4 | + | 1.1 | 1.2 |
| 6634.1.7 | + | 1.2 | 1.2 |
| 6634.2.1 | + | 1.3 | 0.9 |
| 6634.2.3 | + | 1.2 | 1.2 |
| 6634.2.7 | + | 1.4 | 0.7 |
| 6634.2.9 | + | 1.1 | 0.6 |
| 6634.2.10 | + | 1.4 | 0.9 |
| 6634.2.24 | + | 1.2 | 0.9 |
| 6634.2.25 | + | 1.2 | 0.9 |
| 6634.2.26 | + | 1.0 | 1.3 |
| 6634.3.1 | + | 1.4 | 0.7 |
| 6634.3.2 | + | 1.5 | 0.8 |
| 6634.3.4 | + | 1.3 | 0.9 |
| 6634.3.6 | + | 1.2 | 0.8 |
| 6634.3.8 | + | 1.4 | 0.7 |
| 6634.3.9 | + | 1.2 | 1.0 |
| 6634.3.13 | + | 1.4 | 0.7 |
| 6634.4.3 | + | 1.1 | 0.8 |
| 6634.4.10 | + | 1.3 | 0.9 |
| 6634.4.12 | + | 1.4 | 0.7 |
| 6634.4.13 | + | 1.2 | 0.8 |
| 6634.4.16 | + | 0.9 | 0.6 |
| 6634.4.17 | + | 1.1 | 0.7 |
| 6634.5.4 | + | 1.3 | 1.0 |

TABLE 1-continued

Relative transgene copy numbers and GFP expression of ATPS:GFP transgenic plants

| Clone ID | GFP expression | GFP qPCR | HPT qPCR |
| --- | --- | --- | --- |
| 6634.5.11 | + | 1.3 | 1.0 |
| 6634.5.12 | + | 0.9 | 1.7 |
| 6634.6.1 | + | 0.7 | 1.6 |
| 6634.6.3 | + | 0.9 | 2.0 |
| 6634.6.7 | + | 1.3 | 1.2 |

Example 5

Construction of ATPS Promoter Deletion Constructs

Figure 4A:
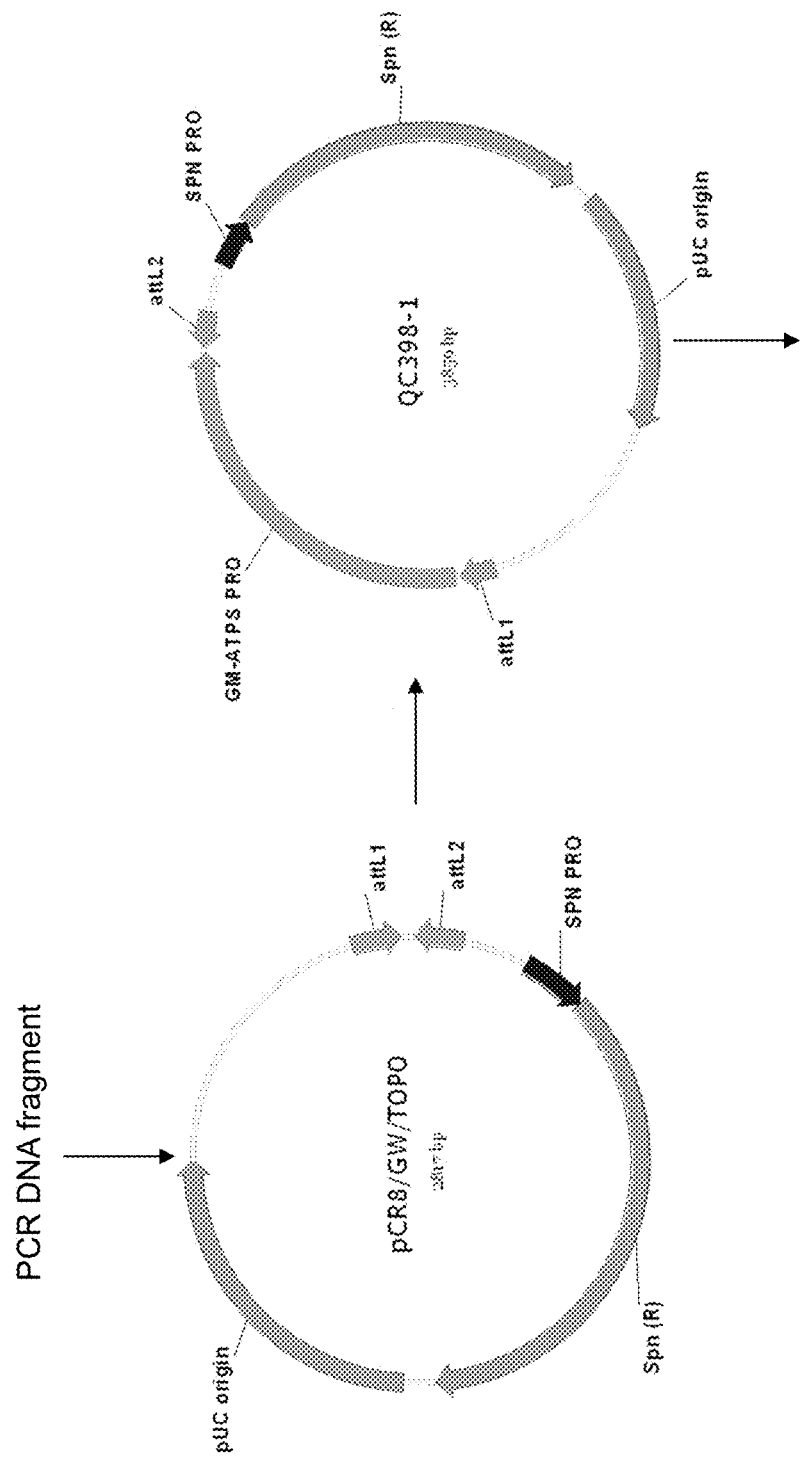
FIG. 4A-4B shows the maps of plasmid pCR8/GW/TOPO, QC398-1, QC330, and QC398-1Y containing the truncated 1042 bp ATPS promoter. Other promoter deletion constructs QC398-2Y, QC398-3Y, QC398-4Y, and QC398-5Y containing the 755, 602, 402, and 228 bp truncated ATPS promoters, respectively, have the same map configuration, except for the truncated promoter sequences.
Figure 4:
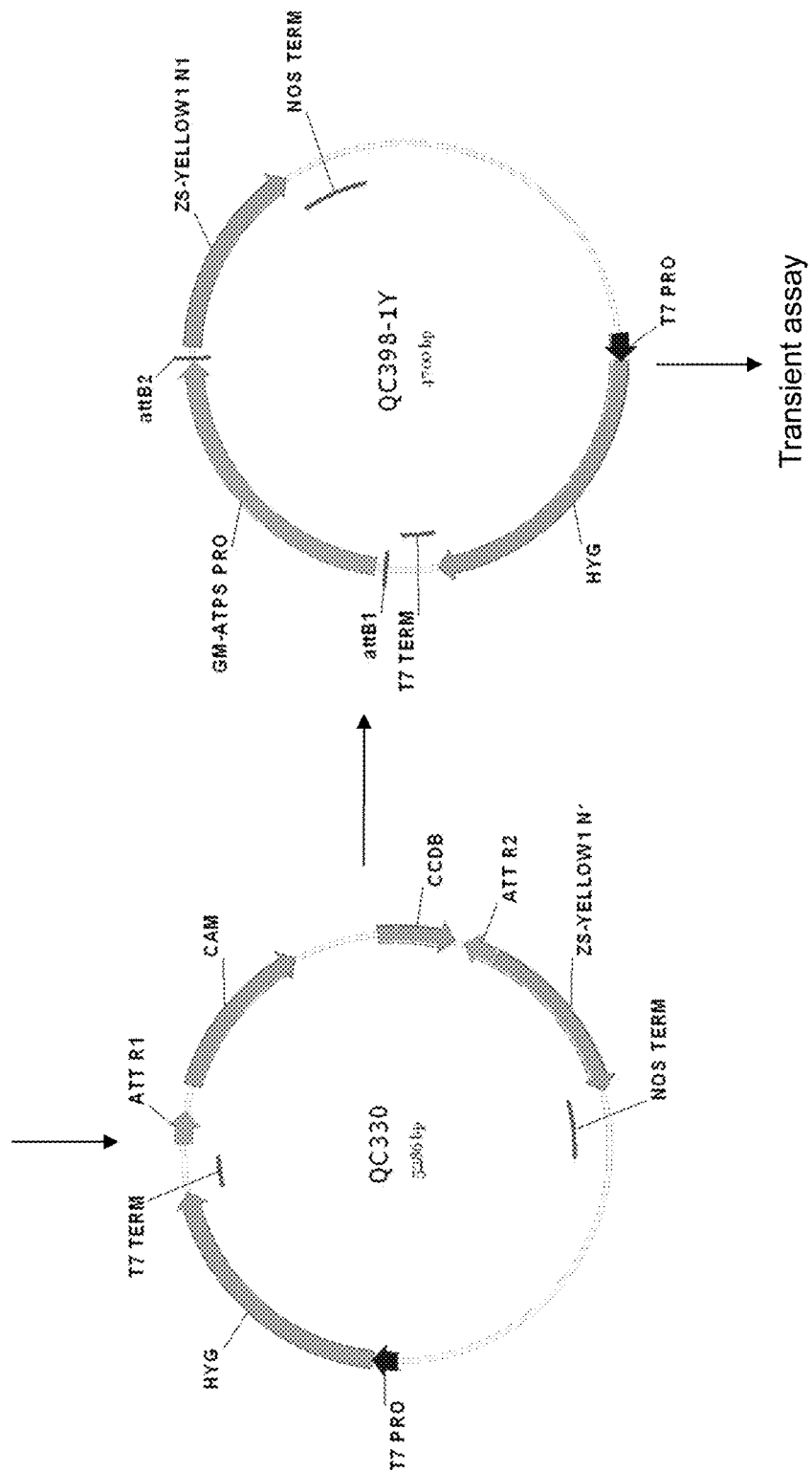

To define the transcriptional elements controlling the ATPS promoter activity, the 1048 bp full length (SEQ ID NO:1) and five 5' unidirectional deletion fragments 755 bp, 602 bp, 402 bp, and 228 bp in length corresponding to SEQ ID NO:2, 3, 4, and 5, respectively, were made by PCR amplification from the full length soybean ATPS promoter contained in the original construct QC398 (FIG. 3B). The same antisense primer QC398-A (SEQ ID NO:11) was used in the amplification by PCR of all the five ATPS promoter fragments (SEQ ID NO: 1, 2, 3, 4, and 5) by pairing with different sense primers SEQ ID NOs:12, 13, 14, 15, and 16, respectively. Each of the PCR amplified promoter DNA fragments was cloned into the GATEWAY® cloning ready TA cloning vector pCR8/GW/TOPO (Invitrogen) and clones with the correct orientation, relative to the GATEWAY® recombination sites attL1 and attL2, were selected by sequence confirmation. The map of construct QC398-1 (SEQ ID NO:24) containing the full length ATPS promoter fragment is shown in FIG. 4A. The maps of constructs QC398-2, 3, 4, and 5 containing the truncated ATPS promoter fragments SEQ ID NOs: 2, 3, 4, and 5 are similar to QC398-1 map and are not shown. The promoter fragment in the right orientation was subsequently cloned into a GATEWAY® destination vector QC330 (SEQ ID NO:25) by GATEWAY® LR Clonase® reaction (Invitrogen) to place the promoter fragment in front of the reporter gene YFP (see the example map QC398-1Y in FIG. 4B). A 21 bp GATEWAY® recombination site attB2 (SEQ ID NO:41) was inserted between the promoter and the YFP reporter gene coding region as a result of the GATEWAY® cloning process. The maps of constructs QC398-2Y, 3Y, 4Y, and 5Y containing the ATPS promoter fragments SEQ ID NOs: 2, 3, 4, and 5 are similar to QC398-1Y map and not shown.

The ATPS:YFP promoter deletion constructs were delivered into germinating soybean cotyledons by gene gun bombardment for transient gene expression study. The full length ATPS promoter in QC398 that does not have the attB2 site located between the promoter and the GFP gene was also included for transient expression analysis as a control. The six ATPS promoter fragments analyzed are schematically described in FIG. 5.

Example 6

Transient Expression Analysis of ATPS:YFP Constructs

The constructs containing the full length and truncated ATPS promoter fragments (QC398, QC398-1Y, 2Y, 3Y, 4Y, and 5Y) were tested by transiently expressing the ZS-GREEN1 reporter gene in QC398 or ZS-YELLOW1 N1 reporter gene in QC398-1Y, 2Y, 3Y, 4Y, and 5Y in germinating soybean cotyledons. Soybean seeds were rinsed with 10% TWEEN® 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 4 except with more DNA (100 ng/μl). The bombardments were also carried out under similar parameters as described in EXAMPLE 4. GFP or YFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification using a Leica DFC500 camera with settings as 0.60 gamma, 1.0× gain, 0.70 saturation, 61 color hue, 56 color saturation, and 0.51 second exposure.

The full length ATPS promoter construct QC398 with GFP and QC398-1Y with YFP both had similar weak yellow fluorescence signals in transient expression assay by showing the small faint yellow dots (shown as faint white dots in FIG. 6) in red background (shown as gray color in FIG. 6) compared with the strong bright dots shown by the positive control construct pZSL90 (shown as bright white dots in FIG. 6). The attB2 site did not seem to interfere with promoter activity and reporter gene expression. Each dot represented a single cotyledon cell which appeared larger if the fluorescence signal was strong or smaller if the fluorescence signal was weak even under the same magnification. The three longer deletions constructs QC398-2Y, 3Y, and 4Y all showed similar weak yellow fluorescence signals comparable to the full length constructs (FIG. 6). The smallest deletion construct QC398-5Y also showed yellow dots (shown as faint white dots in FIG. 6), though smaller, suggesting that as short as 228 bp ATPS promoter sequence upstream of the start codon ATG was long enough for the minimal expression of a reporter gene.

Example 7

ATPS:GFP Expression in Stable Transgenic Soybean Plants

YFP gene expression was tested at different stages of transgenic plant development for green fluorescence emission under a Leica MZFLIII stereo microscope equipped with appropriate fluorescent light filters. Green fluorescence (shown as white areas in FIG. 7) was detected early on during somatic embryo development and throughout all stages of transgenic plant development in most tissues tested, such as somatic embryos, flower, stem, root, pod, and seed. The seed and pod development stages were defined according to descriptions in Fehr and Caviness, IWSRBC 80:1-12 (1977). During tissue culture stages of transgenic plant regeneration, fluorescence was detected in young globular and cotyledon stage somatic embryos (FIG. 7A-C), and in mature embryos (FIG. 7D). The negative section of a positive embryo cluster emitted weak red color (shown as dark grey areas in FIG. 7A-D) due to auto fluorescence from the chlorophyll contained in soybean green tissues including embryos. Negative controls for other tissue types displayed in FIG. 7 are not shown, but any green tissue such as leaf or stem negative for YFP expression would be red and any white tissue such as root and petal would be dull yellowish under the green fluorescent light filter.

Green fluorescence was detected weakly in both the cross and longitudinal sections of stem (FIG. 7I, J) and strongly in root (FIG. K, L) at T0 plant stage. Fluorescence signals seemed to be primarily detected in the vascular bundles of stem and root. Expression was not readily detectable in flower bud (FIG. 7E) or leaf (FIG. 7P) probably due to the limited sensitivity of the fluorescent reporter gene.

A soybean flower consists of five sepals, five petals including one standard large upper petal, two large side petals, and two small fused lower petals called kneel to enclose ten stamens and one pistil. The pistil consists of a stigma, a style, and an ovary in which there are 2-4 ovules. A stamen consists of a filament, and an anther on its tip. Pollen grains reside inside anther chambers and are released during pollination. Fluorescence signals (shown as white areas in FIG. 7) were detected in sepals and slightly in sepals of open flower (FIG. 7F), and strongly in pollen grains and slightly in the fused filaments (FIG. 7G). The bright dots on the stigma and pistil wall are pollen grains. Fluorescence signals were detected in the inner lining of the pistil but not obviously in ovules (FIG. 7H).

Good fluorescence signals were detected in developing seeds and also weakly pods at all stages of the ATPS:GFP transgenic plants from very young R3 pod of ~5 mm long (not shown), to full R4 pod of ~20 mm long (FIG. 7M), until mature R5, R6 pod fully filled with seeds (FIG. 7N, O). Fluorescence signals were detected in both seed coat and embryo especially. Detail descriptions of soybean development stages can be found in (Fehr and Caviness, CODEN: IWSRBC 80:1-12 (1977)). In conclusion, ATPS:GFP expression was detected in most tissues throughout transgenic plant development with preferences in root and seed indicating that the soybean ATPS promoter is a weak constitutive promoter with preferential stronger expression in root and seed.

What is claimed is:

1. A method of expressing a coding sequence or a functional RNA in a plant comprising:
   a) introducing a recombinant DNA construct comprising a nucleotide sequence comprising a sequence selected from the group consisting of SEQ ID NO:1, SEQ ID NO:2, SEQ ID NO:3, SEQ ID NO:4, and SEQ ID NO:5 operably linked to at least one heterologous nucleotide sequence into the plant, wherein said nucleotide sequence is a promoter, wherein the at least one heterologous nucleotide sequence comprises a coding sequence or encodes a functional RNA;
   b) growing the plant of step a); and
   c) selecting a plant displaying expression of the coding sequence or the functional RNA of the recombinant DNA construct.

2. A method of transgenically altering a marketable plant trait, comprising:
   a) introducing a recombinant DNA construct comprising a nucleotide sequence comprising a sequence selected from the group consisting of SEQ ID NO:1, SEQ ID NO:2, SEQ ID NO:3, SEQ ID NO:4, and SEQ ID NO:5 operably linked to at least one heterologous nucleotide sequence into the plant, wherein said nucleotide sequence is a promoter;
   b) growing a fertile, mature plant resulting from step a); and
   c) selecting a plant expressing the at least one heterologous nucleotide sequence in at least one plant tissue based on the altered marketable trait.

3. The method of claim 2 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

4. A method for altering expression of at least one heterologous nucleotide sequence in a plant comprising:
   (a) transforming a plant cell with a recombinant DNA construct comprising a nucleotide sequence comprising a sequence selected from the group consisting of SEQ ID NO:1, SEQ ID NO:2, SEQ ID NO:3, SEQ ID NO:4, and SEQ ID NO:5 operably linked to at least one heterologous nucleotide sequence, wherein said nucleotide sequence is a promoter;
   (b) growing fertile mature plants from transformed plant cell of step (a); and
   (c) selecting plants containing the transformed plant cell wherein the expression of the heterologous nucleotide sequence is increased or decreased.

5. The method of claim 4, wherein the plant is a soybean plant.

6. A plant produced by a method comprising the steps of:
   a) introducing a recombinant DNA construct comprising a nucleotide sequence comprising a sequence selected from the group consisting of SEQ ID NO:1, SEQ ID NO:2, SEQ ID NO:3, SEQ ID NO:4, and SEQ ID NO:5 operably linked to at least one heterologous nucleotide sequence into the plant, wherein said nucleotide sequence is a promoter;
   b) growing a fertile, mature plant resulting from step a); and
   c) selecting a plant expressing the at least one heterologous nucleotide sequence in at least one plant tissue.

7. The plant of claim 6, wherein the plant is a soybean plant.

8. A plant stably transformed with a recombinant DNA construct comprising a soybean constitutive promoter and a heterologous nucleotide sequence operably linked to said constitutive promoter, wherein said constitutive promoter controls expression of said heterologous nucleotide sequence in a plant cell, and further wherein said constitutive promoter comprises a sequence selected from the group consisting of SEQ ID NO:1, SEQ ID NO:2, SEQ ID NO:3, SEQ ID NO:4 and SEQ ID NO:5.

9. The plant of claim 6, 7, or 8, wherein expression of the heterologous nucleotide confers a marketable trait to the plant, wherein the marketable trait is selected from the group consisting of: disease resistance, herbicide resistance, insect resistance, altered carbohydrate metabolism, altered fatty acid metabolism, altered amino acid metabolism, altered plant development, altered plant growth regulation, yield improvement, drought resistance, cold resistance, heat resistance, and salt resistance.

* * * * *